United States Patent
Suzuki et al.

(10) Patent No.: US 7,899,765 B2
(45) Date of Patent: Mar. 1, 2011

(54) METHOD OF MEASURING TASTE USING TWO PHASE RADIAL BASIS FUNCTION NEURAL NETWORKS, A TASTE SENSOR, AND A TASTE MEASURING APPARATUS

(75) Inventors: Koji Suzuki, Yokohama (JP); Saeko Ishihara, Yokohama (JP); Atsushi Ikeda, Yokohama (JP); Yoshio Araki, Yokohama (JP); Kenichi Maruyama, Yokohama (JP); Daniel Citterio, Yokohama (JP); Masafumi Hagiwara, Yokohama (JP)

(73) Assignee: Keio University, Tokyo (JP)

( * ) Notice: Subject to any disclaimer, the term of this patent is extended or adjusted under 35 U.S.C. 154(b) by 571 days.

(21) Appl. No.: 11/920,924

(22) PCT Filed: May 22, 2006

(86) PCT No.: PCT/JP2006/310152
§ 371 (c)(1),
(2), (4) Date: Mar. 25, 2008

(87) PCT Pub. No.: WO2006/126489
PCT Pub. Date: Nov. 30, 2006

(65) Prior Publication Data
US 2009/0234196 A1    Sep. 17, 2009

(30) Foreign Application Priority Data
May 23, 2005   (JP) .................. 2005-149921

(51) Int. Cl.
*G06E 1/00*    (2006.01)
(52) U.S. Cl. .................................................. 706/16
(58) Field of Classification Search ............. 706/10–20
See application file for complete search history.

(56) References Cited

U.S. PATENT DOCUMENTS
6,850,252 B1 *   2/2005   Hoffberg ................... 715/716
(Continued)

FOREIGN PATENT DOCUMENTS
JP      63-241354 A      10/1988
(Continued)

OTHER PUBLICATIONS

Legin et al., "Evaluation of Italian wine by the electronic tongue: recognition, quantitative analysis and correlation with human sensory perception," Analytica Chimica acta, vol. 484, pp. 33-44, 2003.

(Continued)

*Primary Examiner* — David R Vincent
(74) *Attorney, Agent, or Firm* — Birch, Stewart, Kolasch & Birch, LLP

(57) ABSTRACT

A method for measuring tastes, which can better simulate the human gustation than known methods, as well as a taste sensor, computer program and an apparatus for measuring tastes, is disclosed. In this method, data processing is carried out by a two-phase radial basis function neural network. That is, by sensors, each of which sensors can quantify at least one component representing, individually or cooperatively, the taste of saltiness, sourness, sweetness, umami or bitterness, to obtain a response value from each sensor, and each of the obtained response values is input to a first phase radial basis function neural network to calculate the concentration of each component from each response value. Then, the concentration of each component is fed into a second phase radial basis function neural network, which correlates the concentration of each component with the intensities of saltiness, sourness, sweetness, umami and bitterness sensed by humans, to calculate the intensities of saltiness, sourness, sweetness, umami and bitterness sensed by humans.

9 Claims, 21 Drawing Sheets

U.S. PATENT DOCUMENTS

2002/0186875 A1* 12/2002 Burmer et al. ............... 382/133
2007/0053513 A1* 3/2007 Hoffberg ..................... 380/201

FOREIGN PATENT DOCUMENTS

JP          6-174689 A      6/1994

OTHER PUBLICATIONS

Albrecht et al., "Generalized radical basis function networks for classification and novelty detection: self-organization of optimal Bayesian decision," Neural Networks, vol. 13, pp. 1075-1093, 2000.

* cited by examiner before optimization
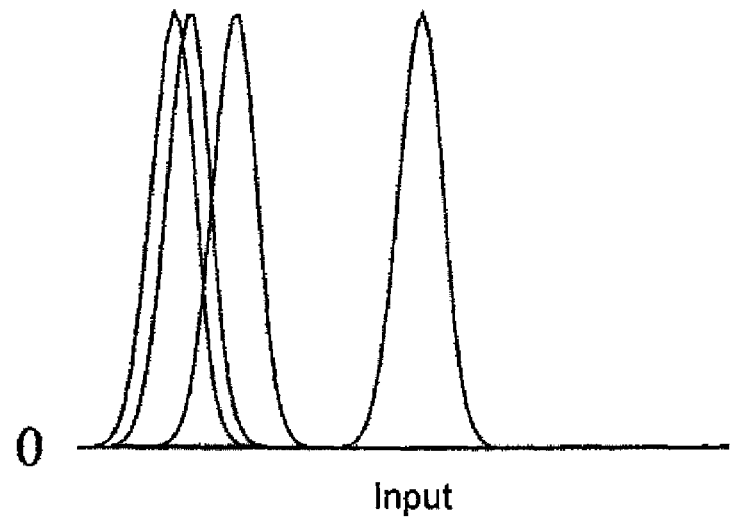
Input
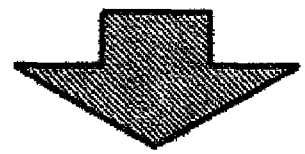
after optimization
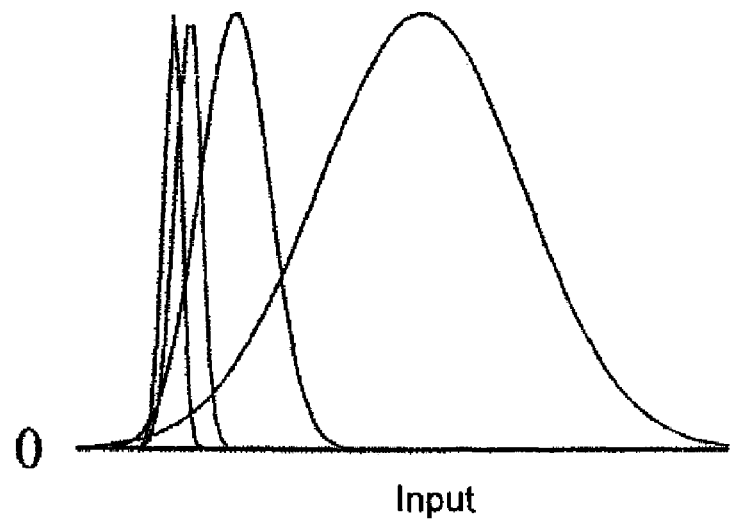
Input
Fig.3

```
Jan 25 2005 17:27                     main.cpp                         Page 1

//RBF
#include <iostream>
#include <fstream>
#include <stdlib.h>
#include <time.h>
include <math.h>
#include "RBF.h"
//using namespace std;

define NORMALIZE_MODE 0//0-as it is   ,1-log,2-sqrt,3-sqrt(sqrt),4- plus-minus inversion int main(int argc, char *argv[]){ int i=0,j=0,l=0;
  int cv=0;

char *input_file_name;
  input_file_name = argv[1];// first argument (input file name)

if(argc!=4){
                cout << "Please fill arguments. [1]input file name [2]input dimension
[3]lambda(weight control)\n";
                return 0;
        }

RBF rbf;
        rbf.input_num = atoi(argv[2]);// second argument (input number of dimensions)
        rbf.CR_count(input_file_name);
        rbf.hidden_num = rbf.column_num-1;// set data set number for CV to -1
        rbf.lambda = atof(argv[3]);// third argument (coefficient lambda in weight-decay term)
        rbf.normalize_mode = NORMALIZE_MODE;

double output_data=0.0;
  double teacher_data=0.0;
  double error = 0.0;

double log_error;
  double **output_sum;
  double **teacher;
  double **error_sum;
  output_sum = new double* [rbf.column_num];
  teacher = new double* [rbf.column_num];
  error_sum = new double* [rbf.column_num];
  for(i=0;i<rbf.column_num;i++){
    output_sum[i] = new double [rbf.output_num];
    teacher[i] = new double [rbf.output_num];
    error_sum[i] = new double [rbf.output_num];
  }
  for(i=0;i<rbf.column_num;i++){
    for(j=0;j<rbf.output_num;j++){
      output_sum[i][j] = 0.0;
      teacher[i][j] = 0.0;
      error_sum[i][j] = 0.0;
    }
  }

// prelearning
  // preparation of output file
        for(i=0;i<rbf.column_num;i++){
                // reset function
                rbf.WL_Init(input_file_name);
                for(j=0;j<(i+1);j++){
                        rbf.CV();
                }
                rbf.Init_Center();//!!
                rbf.Learn();
```

Fig.11

```
Jan 25 2005 17:27                    main.cpp                          Page 2 for(j=0;j<rbf.output_num;j++){
                    output_data = rbf.Reconstruction(rbf.A_Out(rbf.column_num-1,j
),j);
                    teacher_data = rbf.Reconstruction(rbf.teacher_data[rbf.column
_num-1][j],j);
                    if(output_data<0.0){
                            output_data = 0.0;
                    }
                    if(teacher_data!=0.0){
                            error_sum[i][j] = fabs((output_data-teacher_data)/tea
cher_data)*100.0;
                    }
                    else{
                            error_sum[i][j] = fabs(output_data);
                    }
                    cout << output_data << "       " << teacher_data << " ";
                    cout << error_sum[i][j] << "     ";// output of results of prelearning
            }
            cout << "\n";

// release of memory
            rbf.Finalize();
    } log_error = 0.0;
    for(i=0;i<rbf.output_num;i++){
            error = 0.0;
    for(j=0;j<rbf.column_num;j++){
                    error += error_sum[j][i];
            }
            error = error/rbf.column_num;
            cout << "        " << "  " << error << " ";
            log_error+=error;
    }
    cout << log_error << "\n";

for(i=0;i<rbf.column_num;i++){
    delete [] (double *)output_sum[i];
    delete [] (double *)teacher[i];
    delete [] (double *)error_sum[i];
  }
  delete [] output_sum;
  delete [] teacher;
  delete [] error_sum;

return 0;
}
```

Fig.12

```
Jan 26 2005 11:02                    RBF.cpp                         Page 1 include "RBF.h"
//using namespace std;

/*
class RBF{
        int input_num;// number of input layer elements
        int hidden_num;// number of intermediate layer elements
        int output_num;// number of output layer elements
        double **center;// center of RBF
        double **hidden_out;// output of intermediate layer
        double **d_h_out;// for storing hidden_out
        double **d_h_out2;// for storing hidden_out
        double *w_list;//binding load
public:
        int column_num;// number of data sets
        double r;// radius of RBF
        double lambda;// coefficient
        double **input_data;// for storing input
        double *teacher_data;// for storing teacher
        RBF();
        ~RBF();
        double** Inverse_Matrix(double **matrix, int n);// function for obtaining inverse matrix
        void Init_Center();// function generating center of RBF
        double HiddenOut(double *in, double *c);//intermediate layer-deriving function
        void Learn();
        void Initialize(int input, int hidden, int output);// resetting function
        void Finalize();//release of memory
};
*/

RBF::RBF(){
}

RBF::~RBF(){
} void RBF::CR_count(char *file_name){
        int i=0,j=0,k=0,row=0,column=0;
        double num;
        int word_num = 10000;
        char *buf;
        buf = new char [word_num];
        ifstream fin0(file_name);

if(!fin0){
    cout << "cannot open input file name.\n";
    exit(1);
  }
        while(!fin0.eof()){
                if(fin0.getline(buf,word_num)){
                        i++;
                }
        }
        column=i;
        i=0;
        fin0.close();
        ifstream fin1(file_name);// input file name
        while(!fin1.eof()){
                j++;
                fin1 >> num;
        }
        row=(j-1)/column;
        j=0;
        fin1.close();
        delete [] buf;
```

Fig.13

```
Jan 26 2005 11:02                    RBF.cpp                              Page 2
        // substitute numbers of data sets and output
        column_num = column;
        output_num = row - input_num;
        if(input_num<=0){
                cout << "Please set input dimension larger than 0.\n";
                exit(1);
        }
        else if(output_num<=0){
                cout << "Output dimension is fault.\n";
                exit(1);
        }
} double RBF::Reconstruction(double o, int n){
        double out=0.0;
        out = ((o-0.1)*teacher_scale[n]/0.8)+teacher_min[n];
        if(normalize_mode==1){
                out = exp(out);
        }
        else if(normalize_mode==2){
                out = pow(out,2);
        }
        else if(normalize_mode==3){
                out = pow(pow(out,2),2);
        }
        else if(normalize_mode==4){
                out = -out;
        } return out;
} void RBF::Normalization(){
        int i=0,j=0;
        double *min;
        double *max;

//input data
        min = new double [input_num];
        max = new double [input_num];

for(i=0;i<input_num;i++){
                min[i] = 10000.0;
                max[i] = -10000.0;
        }
        for(i=0;i<input_num;i++){
                for(j=0;j<column_num;j++){
                        if(min[i]>input_data[j][i]){
                                min[i] = input_data[j][i];
                        }
                        if(max[i]<input_data[j][i]){
                                max[i] = input_data[j][i];
                        }
                }
        }
        for(i=0;i<input_num;i++){
                for(j=0;j<column_num;j++){
                        input_scale[i] = max[i]-min[i];
                        input_min[i] = min[i];
                        input_data[j][i]=(input_data[j][i]-min[i])/(max[i]-min[i]);
                }
        }
        delete [] min;
        delete [] max;

// teacher data
```

Fig.14

```
Jan 26 2005 11:02                    RBF.cpp                         Page 3 min = new double [output_num];
        max = new double [output_num];

for(i=0;i<output_num;i++){
                min[i] = 10000.0;
                max[i] = -10000.0;
        }
        for(i=0;i<output_num;i++){
                for(j=0;j<column_num;j++){
                        if(normalize_mode==1){
                                teacher_data[j][i] = log(teacher_data[j][i]);//log
                        }
                        else if(normalize_mode==2){
                                teacher_data[j][i] = sqrt(teacher_data[j][i]);//sqrt
                        }
                        else if(normalize_mode==3){
                                teacher_data[j][i] = sqrt(sqrt(teacher_data[j][i]));/
/sqrt(sqrt)
                        }
                        else if(normalize_mode==4){
                                teacher_data[j][i] = -teacher_data[j][i];//-
                        }
                }
        }
        for(i=0;i<output_num;i++){
                for(j=0;j<column_num;j++){
                        if(min[i]>teacher_data[j][i]){
                                min[i] = teacher_data[j][i];
                        }
                        if(max[i]<teacher_data[j][i]){
                                max[i] = teacher_data[j][i];
                        }
                }
        }
        for(i=0;i<output_num;i++){
                for(j=0;j<column_num;j++){
                        teacher_scale[i] = max[i]-min[i];
                        teacher_min[i] = min[i];
                        teacher_data[j][i]=0.8*(teacher_data[j][i]-min[i])/(max[i]-mi
n[i])+0.1;
                }
        }
        delete [] min;
        delete [] max;
} void RBF::FileIO(char *f_name){
        int i=0,j=0;
        double *data_list;
  data_list = new double [(input_num+output_num)*column_num];

char *file_name;
        file_name = f_name;

ifstream fin(file_name);// filename if(!fin){
   cout << "Cannot open input_file.\n";
   exit(1);
}
i = 0;
while(!fin.eof()){
   fin >> data_list[i];
   i++;
}
   fin.close();
```

Fig.15

```
Jan 26 2005 11:02                    RBF.cpp                           Page 4
//completion of input and output file
  for(i=0;i<column_num;i++){
     for(j=0;j<input_num;j++){
        input_data[i][j] = data_list[(input_num+output_num)*i+j];
     }
              for(j=0;j<output_num;j++){
                        teacher_data[i][j] = data_list[(input_num+output_num)*i+input
_num+j];
                     if(normalize_mode==1&&teacher_data[i][j]==0.0){
                             cout << "Warning!! log normalization with teacher=0.0
!\n";
                             exit(1);
                     }
              }
     }
     delete [] data_list;
}
// function forming center of RBF from input data
//center[hidden_num][input_num] | input_data[column_num][input_num]
void RBF::Init_Center(){
     int i=0,j=0,k=0;

double min_r=10000.0;// r[i] is minimum other than 0
     for(i=0;i<hidden_num;i++){
           for(j=0;j<input_num;j++){
                 center[i][j] = input_data[i][j];
           }
     }
     double *average;
     double sum=0.0;

for(i=0;i<hidden_num;i++){
           r[i] = 0.0;
     }
     average = new double [input_num];// store average of data
     for(i=0;i<input_num;i++){
           average[i]=0.0;
     }
     for(i=0;i<input_num;i++){
           for(j=0;j<hidden_num;j++){
                 average[i]+=center[j][i];
           }
           average[i] = (double)average[i]/hidden_num;
     }
     for(i=0;i<hidden_num;i++){
           for(j=0;j<input_num;j++){
                 r[i] += pow((center[i][j]-average[j]),2);
           }
           r[i] = sqrt(r[i]);
           if(min_r>r[i]&&r[i]!=0.0){
                 min_r = r[i];
           }
     }
     // action when r[i]==0.0
     for(i=0;i<hidden_num;i++){
           if(r[i]==0.0){
                 r[i]!=min_r;
           }
     }
     delete [] average;

//fixed_r
     // recently find dots
     /*
     double *d_min,dd=0.0;
```

Fig.16

```
        d_min = new double [hidden_num];
        for(i=0;i<hidden_num;i++){
                d_min[i] = 10000.0;
        }
        for(k=0;k<hidden_num;k++){
                for(i=0;i<hidden_num;i++){
                        if(i!=k){
                                dd = 0.0;
                                for(j=0;j<input_num;j++){
                                        dd += pow(center[k][j]-center[i][j],2);
                                        cout << center[i][j] << "\n";
                                }
                                //cout << dd << "\n";
                                if(d_min[k] >dd){
                                        d_min[k]=dd;
                                }
                        }
                }
        } dd = 0.0;
        for(i=0;i<hidden_num;i++){
                dd += d_min[i];
        }
    dd = dd/hidden_num;
        for(i=0;i<hidden_num;i++){
                r[i] = dd;
        }
        delete [] d_min;*/
}
void RBF::WL_Init(char *f_name){ int i=0,j=0,l=0;
        srand((unsigned)time(NULL));

char *file_name;
        file_name = f_name;

// secure memory
        input_data = new double* [column_num];
        teacher_data = new double* [column_num];

for(i=0;i<column_num;i++){
                input_data[i] = new double [input_num];
                teacher_data[i] = new double [output_num];
        }
        r = new double [hidden_num];

input_scale = new double [input_num];
        input_min = new double [input_num];
        teacher_scale = new double [input_num];
        teacher_min = new double [input_num];

center = new double* [hidden_num];
        hidden_out = new double* [hidden_num];
        w_list = new double* [hidden_num];

for(i=0;i<hidden_num;i++){
                center[i] = new double [input_num];
                hidden_out[i] = new double [column_num];
                w_list[i] = new double [output_num];
        }

// resetting
        for(i=0;i<column_num;i++){
```

Fig.17

```
Jan 26 2005 11:02                    RBF.cpp                              Page 6 for(j=0;j<input_num;j++){
                        input_data[i][j] = 0.0;
                }
                for(j=0;j<output_num;j++){
                        teacher_data[i][j] = 0.0;
                }
        }

FileIO(file_name);// input file for(i=0;i<hidden_num;i++){
                for(j=0;j<column_num;j++){
                        hidden_out[i][j] = 0.0;
                }
        } for(i=0;i<hidden_num;i++){
                for(j=0;j<output_num;j++){
                        w_list[i][j] = 0.0;
                }
        }

// normalization of data
        Normalization();
}
double RBF::A_Out(int k, int output){
  int i=0,j=0;
  double sum=0.0;

double output_data=0.0;
        for(i=0;i<hidden_num;i++){
    for(j=0;j<input_num;j++){
       sum += (double)pow((input_data[k][j] - center[i][j]),2);
    }
                hidden_out[i][k] = exp(-(sum/(r[i]*r[i])));//output of intermediate layer element i
                sum = 0.0;
        }
        for(i=0;i<hidden_num;i++){
                output_data += hidden_out[i][k]*w_list[i][output];
        }
        return output_data;
}
// all data are shifted by one, and head data are moved to rearmost
void RBF::CV(){
        int i=0,j=0;
        double *cv_input;
        cv_input = new double [input_num];
        double *cv_teacher;
        cv_teacher = new double [output_num];

for(i=0;i<input_num;i++){
                cv_input[i] = 0.0;
        }
        for(i=0;i<output_num;i++){
                cv_teacher[i] = 0.0;
        }

// 0th data are retracted for CV
        for(i=0;i<input_num;i++){
                cv_input[i] = input_data[0][i];
        }
        for(i=0;i<output_num;i++){
                cv_teacher[i] = teacher_data[0][i];
        }
```

Fig.18

```
// shift data up to column_num-1 by one
for(i=0;i<column_num-1;i++){
        for(j=0;j<input_num;j++){
                input_data[i][j] = input_data[i+1][j];
        }
        for(j=0;j<output_num;j++){
                teacher_data[i][j] = teacher_data[i+1][j];
        }
}
//0th data are shifted to column_num-1
for(i=0;i<input_num;i++){
        input_data[column_num-1][i] = cv_input[i];
}
for(i=0;i<output_num;i++){
        teacher_data[column_num-1][i] = cv_teacher[i];
} delete [] cv_input;
delete [] cv_teacher;
}

// multiplication of matrix (matrix A, row of A, column of A, matrix B, row of B, column of B)
void RBF::Array_Mul(double **a, int Ha, int Va, double **b, int Hb, int Vb, double **matrix){
        if(Ha==0||Va==0||Hb==0||Vb==0){
                cout << "no match 0!\n";
                exit(1);
        }
        if(Ha!=Vb){
                cout << "Ha is not equal to Vb!\n";
                exit(1);
        }
        double **c;
        int i=0,j=0,k=0;

for(i=0;i<Hb;i++){
                for(j=0;j<Va;j++){
                        matrix[i][j] = 0.0;
                        for(k=0;k<Ha;k++){
                                matrix[i][j] += a[k][j]*b[i][k];
                        }
                }
        }
}

// H matrix-forming function (intermediate layer output-deriving function)
// part of RBF (determination of r)
void RBF::HiddenOut(){
  srand((unsigned)time(NULL));
        int i=0,j=0,k=0;
        double sum=0.0;

for(i=0;i<hidden_num;i++){
                for(j=0;j<column_num;j++){
                        for(k=0;k<input_num;k++){
                                sum += (double)pow((input_data[j][k] - center[i][k]), 2);
                        }
                        hidden_out[i][j] = exp(-(sum/(r[i]*r[i])));
                        sum = 0.0;
                }
        }
}
//
```

Fig.19

```
void RBF::Learn(){
        int i=0,j=0,k=0;

for(i=0;i<hidden_num;i++){
                for(j=0;j<output_num;j++){
                        w_list[i][j] = 0.0;
                }
        } d_h_out = new double* [hidden_num];
        d_h_out2 = new double* [column_num];
        for(i=0;i<hidden_num;i++){
                d_h_out[i] = new double [hidden_num];
        }
        for(i=0;i<column_num;i++){
                d_h_out2[i] = new double [hidden_num];
        }
        for(i=0;i<hidden_num;i++){
                for(j=0;j<hidden_num;j++){
                        d_h_out[i][j] = 0.0;
                }
        }
        for(i=0;i<column_num;i++){
                for(j=0;j<hidden_num;j++){
                        d_h_out2[i][j] = 0.0;
                }
        }

// for CV
        column_num--;

// forming H matrix
        HiddenOut(); // substitute value for hidden_out

// calculation of H^t*H
        double **hidden_out2;
        hidden_out2 = new double* [column_num];
        for(i=0;i<column_num;i++){
                hidden_out2[i] = new double [hidden_num];
        }
        for(i=0;i<hidden_num;i++){
                for(j=0;j<column_num;j++){
                        hidden_out2[j][i] = hidden_out[i][j];
                }
        }

Array_Mul(hidden_out2,column_num,hidden_num,hidden_out,hidden_num,column_num,d_h_out);

for(i=0;i<hidden_num;i++){
                d_h_out[i][i] += lambda;
        }

//(H^t*H+ λ )^-1
        Inverse_Matrix(d_h_out,hidden_num); // conversion to inverse matrix //((H^t*H+ λ )^-1)*H^t
        Array_Mul(d_h_out,hidden_num,hidden_num,hidden_out2,column_num,hidden_num,d_h_out2);

double **teacher_data2;
        double **w_list2;
        teacher_data2 = new double* [output_num];
        w_list2 = new double* [output_num];
        for(i=0;i<output_num;i++){
                teacher_data2[i] = new double [column_num];
```

Fig.20

```
                w_list2[i] = new double [hidden_num];
        }
        for(i=0;i<output_num;i++){
                for(j=0;j<column_num;j++){
                        teacher_data2[i][j] = 0.0;
                }
                for(j=0;j<hidden_num;j++){
                        w_list2[i][j] = 0.0;
                }
        }
        for(i=0;i<column_num;i++){
                for(j=0;j<output_num;j++){
                        teacher_data2[j][i] = teacher_data[i][j];
                }
        }

//((H^t*H+ λ )^-1)*H^t*y
        Array_Mul(d_h_out2,column_num,hidden_num,teacher_data2,output_num,column_num,
w_list2);//teacher!!&w_list!!

for(i=0;i<hidden_num;i++){
                for(j=0;j<output_num;j++){
                        w_list[i][j] = w_list2[j][i];
                }
        } for(i=0;i<output_num;i++){
                delete [] (double *)teacher_data2[i];
                delete [] (double *)w_list2[i];
        }
        delete [] teacher_data2;
        delete [] w_list2;
        for(i=0;i<column_num;i++){
                delete [] (double *)hidden_out2[i];
        }
        delete [] hidden_out2;
        //
        column_num++;

for(i=0;i<hidden_num;i++){
                delete [] (double *)d_h_out[i];
        }
        for(i=0;i<column_num;i++){
                delete [] (double *)d_h_out2[i];
        }
        delete [] d_h_out;
        delete [] d_h_out2;
}
// function for obtaining inverse matrix (only the matrix wherein the numbers of rows and columns are identical)
void RBF::Inverse_Matrix(double **matrix, int n){
        int i=0,j=0,k=0,l=0,x=0,y=0;
        double **a;//store matrix carrying out inverse matrix
        a = new double* [n];
        for(i=0;i<n;i++){
                a[i] = new double [n];
        }
        for(i=0;i<n;i++){
                for(j=0;j<n;j++){
                        a[i][j] = matrix[i][j];
                        matrix[i][j] = 0.0;
                }
        }
        for(i=0;i<n;i++){
                matrix[i][i] = 1.0;
        }
```

Fig.21

```
Jan 26 2005 11:02                    RBF.cpp                          Page 10
        for(i=0;i<n;i++){
                //---b
                for(j=0;j<n;j++){
                        matrix[i][j] = matrix[i][j]/a[i][i];
                }
                //---a
                for(j=i;j<n;j++){
                        if(j!=i){
                                a[i][j] = a[i][j]/a[i][i];
                        }
                }
                //---b
                for(k=0;k<n;k++){
                        if(k!=i){
                                for(j=0;j<n;j++){
                                        matrix[k][j] = matrix[k][j]-(a[k][i]*matrix[i][j]);
                                }
                        }
                }
                //---a
                a[i][i] = 1.0;
                if(i!=n-1){
                        for(k=0;k<n;k++){
                                if(i!=k){
                                        for(j=i+1;j<n;j++){
                                                a[k][j] = a[k][j]-(a[k][i]*a[i][j]);
                                        }
                                        a[k][i] = 0.0;
                                }
                        }
                }
        }
        for(i=0;i<n;i++){
                delete [] (double *)a[i];
        }
        delete [] a;
}

// release of memory
void RBF::Finalize(){
        int i=0,j=0;

for(i=0;i<hidden_num;i++){
                delete [] (double *)center[i];
                delete [] (double *)hidden_out[i];
                delete [] (double *)w_list[i];
        } for(i=0;i<column_num;i++){
                delete [] (double *)input_data[i];
                delete [] (double *)teacher_data[i];
        } delete [] input_data;
        delete [] teacher_data;

delete [] r;
        delete [] center;
        delete [] hidden_out;
        delete [] w_list;

delete [] input_scale;
        delete [] input_min;
        delete [] teacher_scale;
        delete [] teacher_min;
```

Fig.22

Figure 23:
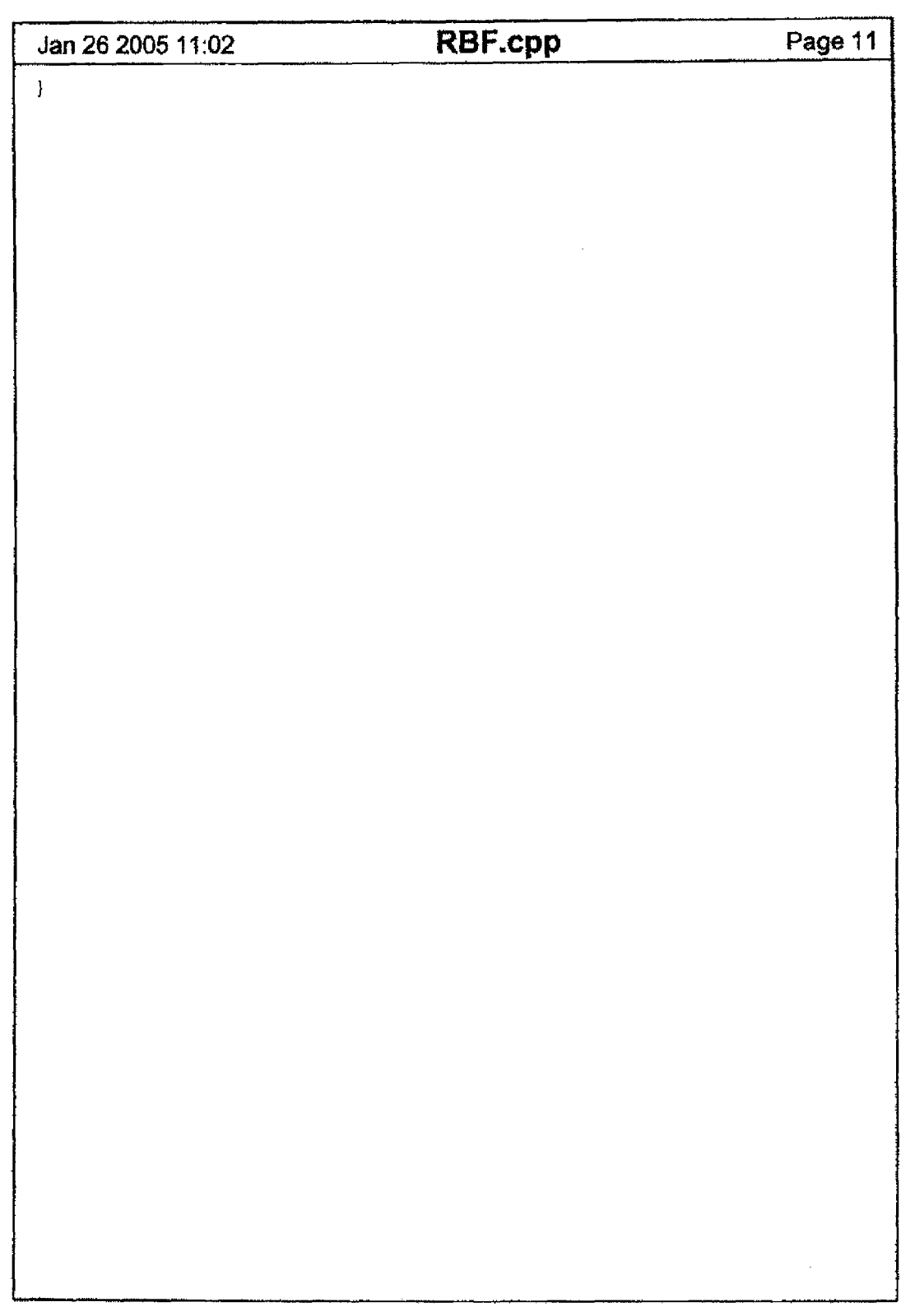

| Jan 26 2005 11:02 | RBF.cpp | Page 11 |

```
Jan 25 2005 13:33                    RBF.h                              Page 1 include <stdlib.h>
include <fstream>
#include <iostream>
#include <time.h>
include <math.h> class RBF{
        double **center;// center of RBF
        double **hidden_out;// output intermediate layer
        double **d_h_out;// for storing hidden_out
        double **d_h_out2;// for storing hidden_out
        double **w_list;//binding load
        double *output_data;// output of network
        double *r;// radius of RBF
        double *input_scale;
        double *input_min;
        double *teacher_scale;
        double *teacher_min;
public:
        int normalize_mode;// normalization mode
        int input_num;// number of input layer elements
        int hidden_num;//number of intermediate layer elements
        int output_num;// number of output layer elements
        int e_column_num;// number of increased layer
        int column_num;// number of data sets (after increase in data, the number becomes equal to e_column_num)
        int data_accession;
        double lambda;// decay term coefficient
        double lambdaD;// learning coefficient
        double lambdaE;// error coefficient when data increased
        double **input_data;// for storing input
        double **teacher_data;// for storing teacher
        RBF();
        ~RBF();
        void CR_count(char *file_name);//count numbers of rows and columns of file
        void Normalization();//normalization of data
        double Reconstruction(double o, int n);//restoration of data
        void FileIO(char *f_name);//input file
        void WL_Init(char *f_name);//resetting function
        void Dr(int n);//dr
        void Dcenter(int n);//dcenter
        void Dw(int n);//dw
        double A_HiddenOut(int k,int hidden);//k->input,hidden->hidden
        double A_Out(int n,int output);//output when input is nth
        void CV();//cv
        void CV_Out();//output for CV
        void Array_Mul(double **a, int Ha, int Va, double **b, int Hb, int Vb ,double
**matrix);// multiplication of matrix (matrix A, row of A, column of A, matrix B, row of B, column of B)
        void Output_Data();//
        void Inverse_Matrix(double **matrix, int n);//output layer output function
        void Init_Center();//function for obtaining inverse matrix
        void HiddenOut();// H matrix-forming function (intermediate layer-deriving function), part of RBF
        void Learn();         (determination of r)
        void Initialize(int input, int hidden, int output);// resetting function
        void Finalize();//release of memory
};
```

Fig.24

METHOD OF MEASURING TASTE USING TWO PHASE RADIAL BASIS FUNCTION NEURAL NETWORKS, A TASTE SENSOR, AND A TASTE MEASURING APPARATUS

TECHNICAL FIELD

The present invention relates to a method for measuring tastes, a taste sensor therefore, and an apparatus for measuring tastes.

BACKGROUND ART

Tastes are measured in various situations, such as encountered in the food industry, clinical sites and others. Up to now, most of the taste measurements are carried out as taste tests relying on human gustation. However, due to the judgments being made by humans, the results vary depending on the individual human taster. The influences of the physical and psychological conditions of the human tasters, as well as blunting of the sense of taste in case of continuous measurements, cannot be ignored. Thus, a taste sensor, which can quantify the tastes sensed by humans more objectively and free from the above-mentioned influences is required.

In order for a taste sensor to simulate the human gustation system, it is not sufficient that the taste sensor can classify and identify the samples, but it is additionally required that the taste sensor can quantify the intensities of the tastes which humans actually sense. To achieve a taste sensor, the sensor is required to have a correlation with human gustation, and to be able to qualitatively and quantitatively analyze the tastes (Non-patent Literature 1). Toko et al. developed a taste sensor which quantifies the tastes of samples (Non-patent Literature 2) This multi-channel taste sensor comprises electrodes having a lipid/polymer membrane, and creates different response patterns for chemical substances having different tastes. The output signals are quantitative.

Patent Literature 1: WO 03/044498 A1
Non-patent Literature 1: Legin, A.; Rudnitskaya, A.; Lvova, L.; Vlasov, Y.; Natale, C. D.; D'Amico, A. Anal. Chim. Acta 2003, 484, 33-44.
Non-patent Literature 2: Toko, K. Meas. Sci. Technol. 1998, 9, 1919-1936.
Non-patent Literature 3: Meng Joo et al., IEEE Transactions on Neural Networks, vol. 13, N03, pp 697-710, MAY 2002
Non-patent Literature 4: S. A. Billing et al., Mechanical Systems and Signal Processing, Vol 13(2), pp. 335-349, 1999
Non-patent Literature 5: Keun Burn Kim et al., Information Sciences, vol. 130, p165-183, 2000
Non-patent Literature 6: M. Marinaro et al, Neural Networks, vol. 13, pp. 719-729, 2000
Non-patent Literature 7: S. Alberecht, Neural Networks, vol. 13, pp. 1075-1093, 2000
Non-patent Literature 8: Masatoshi SAKAWA et al., "Introduction to Neuro Computing" Morikita Publishing Co., Ltd., 1999

DISCLOSURE OF THE INVENTION

Problems to be Solved by the Invention

With the known taste sensors, the degree of correctness of the simulation of human gustation is not satisfactory. For example, they cannot reproduce illusions such as that umami is increased as salt increases, and that bitterness is decreased as sugar increases.

Accordingly, an objective of the present invention is to provide a method for measuring tastes, which can better simulate the human gustation than known methods, as well as a taste sensor therefore, a computer program and an apparatus for measuring tastes.

Means for Solving the Problems

The present inventors intensively studied to discover that human gustation can be well simulated by a method wherein for sensors, each of which sensors can quantify at least one component representing, individually or cooperatively, the taste of saltiness, sourness, sweetness, umami or bitterness, a response value from each sensor is obtained, and each of the obtained response values is fed into a first phase radial basis function neural network to calculate the concentration of each component from each response value; then the concentration of each component is fed into a second phase radial basis function neural network, which correlates the concentration of each component with the intensities of saltiness, sourness, sweetness, umami and bitterness sensed by humans, in order to calculate the intensities of saltiness, sourness, sweetness, umami and bitterness sensed by humans, thereby completing the present invention.

That is, the present invention provides a method for measuring tastes, said method comprising the steps of: subjecting a test sample to measurements by sensors, each of which sensors can quantify at least one component representing, individually or cooperatively, the taste of saltiness, sourness, sweetness, umami or bitterness, to obtain a response value from each sensor; feeding each of the obtained response values into a first phase radial basis function neural network, which correlates each response value with the concentration of each of the components and calculates the concentration of each component from each response value; and feeding the concentration of each component into a second phase radial basis function neural network, which correlates the concentration of each component with the intensities of saltiness, sourness, sweetness, umami and bitterness sensed by humans, to calculate the intensities of saltiness, sourness, sweetness, umami and bitterness sensed by humans. The present invention also provides a taste sensor for carrying out the above-described method according to the present invention, said taste sensor comprising sensors, each of which sensors can quantify at least one component representing, individually or cooperatively, the taste of saltiness, sourness, sweetness, umami or bitterness, to obtain a response value from each sensor. The present invention further provides a computer program for carrying out the above-described method according to the present invention, said computer program comprising a first phase radial basis function neural network, which correlates each response value with the concentration of each of the components and calculates the concentration of each component from each response value; and a second phase radial basis function neural network, which correlates the concentration of each component with the intensities of saltiness, sourness, sweetness, umami and bitterness sensed by humans, to calculate the intensities of saltiness, sourness, sweetness, umami and bitterness sensed by humans. The present invention still further provides an apparatus for measuring tastes, said apparatus comprising the above-described taste sensor according to the present invention and a computer storing the above-described computer program according to the present invention.

Effects of the Invention

By the present invention, a method for measuring tastes, which can better simulate the human gustation than known methods, as well as a taste sensor therefore, a computer program and an apparatus for measuring tastes are provided. By the method of the present invention, not only the 5 tastes, that are, saltiness, sourness, sweetness, umami and bitterness can be qualitatively and quantitatively expressed, but also taste illusions sensed by humans, such as the increase of umami by the addition of salt, and the decrease of bitterness by the increase of sugar, can be measured, so that the human gustation can be more sophisticatedly simulated than by the known methods. Therefore, it is expected that the present invention will contribute to the measurements of tastes in various situations, such as encountered in the food industry, clinical sites and others.

BRIEF DESCRIPTION OF THE DRAWINGS

FIG. 3 explains the concept of basis-auto-optimization.
FIG. 11 shows the source code of the neural network used in the Examples.
FIG. 12 is the continuation of FIG. 11.
FIG. 13 is the continuation of FIG. 12.
FIG. 14 is the continuation of FIG. 13.
FIG. 15 is the continuation of FIG. 14.
FIG. 16 is the continuation of FIG. 15.
FIG. 17 is the continuation of FIG. 16.
FIG. 18 is the continuation of FIG. 17.
FIG. 19 is the continuation of FIG. 18.
FIG. 20 is the continuation of FIG. 19.
FIG. 21 is the continuation of FIG. 20.
FIG. 22 is the continuation of FIG. 21.
FIG. 23 is the continuation of FIG. 22.
FIG. 24 is the continuation of FIG. 23.

BEST MODE FOR CARRYING OUT THE INVENTION

Figure 1:
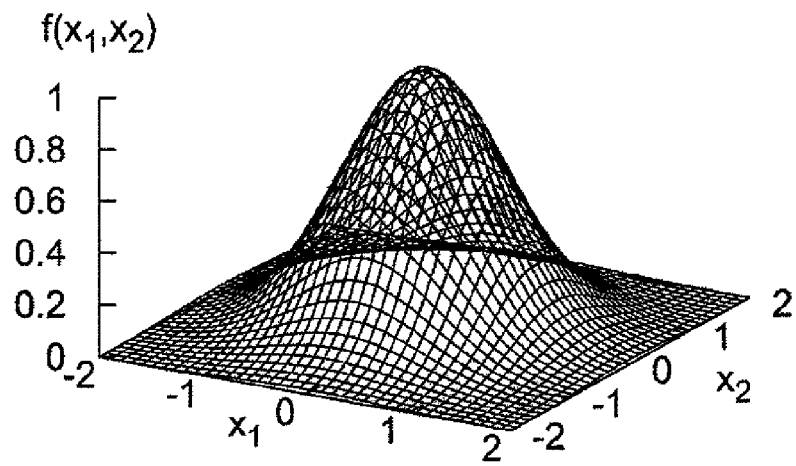
FIG. 1 shows the shape of a RBF.

In the first step of the present invention, a response value from each sensor is obtained by sensors, each of which can quantify at least one component representing, individually or cooperatively, the taste of saltiness, sourness, sweetness, umami or bitterness. Saltiness, sourness, sweetness, umami and bitterness are known as the 5 basic tastes which humans sense. The components which represent the taste of saltiness include NaCl, KCl, LiCl and the like, with NaCl and KCl being preferred. These can be quantified by measuring $Na^+$, $K^+$ and $Cl^-$. The components which represent the taste of sourness include $H^+$ originating from hydrochloric acid, acetic acid, citric acid, malic acid, succinic acid or the like, with $H^+$ being preferred. The components which represent the taste of sweetness include glucose, sucrose, fructose, maltose, glycine, aspartame and the like, with glucose and sucrose being preferred. The components which represent the taste of umami include glutamate, inosinic acid and guanylic acid, with glutamate being preferred. The components which represent the taste of bitterness include caffeine, quinine, tannin, phenylalanine, $Mg^{2+}$ and the like, with caffeine being preferred. The component(s) representing each taste may be either one single component which represents the taste individually, or a plurality of components which cooperatively represent the taste. Therefore, the component(s) may be either one type of component or a plurality of components. In the preferred Examples hereinbelow described, $Na^+$, $K^+$ and $Cl^-$ were selected as the components representing saltiness; $H^+$ was selected as the component representing sourness; glucose and sucrose were selected as the components representing sweetness; glutamate was selected as the component representing umami; and caffeine was selected as the component representing bitterness.

In the first step of the present invention, a test sample is subjected to measurements using the sensors, each of which sensor can quantify the respective above-mentioned component. The term "a sensor which can quantify the respective component" herein means that the sensor can quantify the component in cases where the component is contained individually. A variety of such sensors is known and commercially available, and commercially available sensors may be employed. In the preferred Examples hereinbelow described, 8 types of sensors, which can quantify totally 8 types of components, respectively, that are, the above-mentioned $Na^+$, $K^+$, $Cl^-$, $H^+$, glucose, sucrose, glutamate and caffeine, were used, and each of the sensors was commercially available or prepared by a conventional method from commercially available reagents.

Most beverages and food products contain materials originating from a living organism, and contain various substances, which compositions are unknown. Although known sensors can quantify the above-described respective taste-representing components individually, the selectivity to the respective component is not necessarily satisfactory. Further, as for the sensors using an enzyme, since the enzyme activity is influenced by pH, even if response values are obtained by applying the respective sensors to an actual beverage or food product containing various components, the obtained response values are not thought to correctly indicate the respective components. That is, there is the probability that the response values are influenced by components other than the taste-representing component of interest, and non-negligible errors. Thus, in the method of the present invention, the response values obtained by applying the respective sensors to the test sample are not utilized as the concentrations of the respective components, but the respective response values are fed into a radial basis function neural network (hereinafter also referred to as "RBFN") which is a type of neural network.

The present inventors earlier invented a method for measuring concentrations of a plurality of chemical substances utilizing back propagation neural networks, which are a type of neural network and filed a patent application (Patent Literature 1). Although the first step of the present invention is identical to the method of Patent Literature 1 in respect that the response values from the respective sensors are processed using a neural network to calculate the concentrations of the respective components, in the method of the present invention, RBFN is used as the neural network. Regarding the method described in Patent Literature 1, although various chemical substances can be quantified at one time, the method has drawbacks in that there are some cases in which the stability is not very satisfactory, and that the learning is time-consuming. The cause of these drawbacks is the fact that a back propagation neural network (BPNN) is used for the analysis. BPNN has the following problems.

The number of appropriate learning epochs is unknown, and sufficient leaning is time-consuming.

Since the solution depends on the initial value, the solution tends to be a local solution.

Overlearning is likely to occur.

The term "overlearning" herein means the phenomenon that the network is excessively adapted to the learned data and that its generalizing ability is lost.

Figure 2:
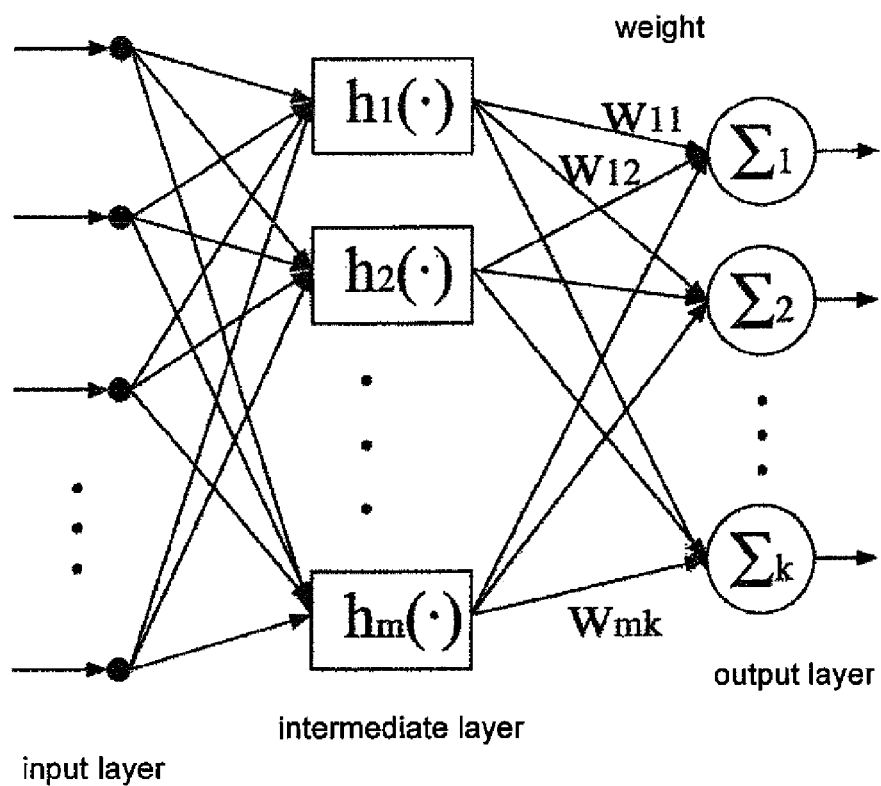
FIG. 2 shows a model of a RBFN.

To solve these problems, RBFN is used in the method of the present invention. RBFN per se is well-known (Non-patent Literature 1). It is known that its processing speed is high and that it is free from the dependence on the initial value (Non-patent Literature 3 to 8). RBFN is a method developing a nonlinear function relying on a radial basis function (RBF), and is usually applied for the approximation of mathematical functions and in pattern recognition (Non-patent. Literature 7 and 8). A representative shape of the RBF is shown in FIG. 1. A network model of RBFN is shown in FIG. 2. RBF is a function having circular contour lines, and the value monotonously decreases as the distance from the center point increases. Representative RBFs include Gaussian functions, In the Examples below, a Gaussian function is utilized. In RBFN, a RBF is used as the output function of the intermediate layer elements, that is, as the basis. The output h(x) of the intermediate layer elements of a RBF is given by the following equation:

$$h(x) = \exp\left(-\frac{\|x-c\|}{r^2}\right) \quad (2.1)$$

wherein $x \in R^n$ represents the input vector, $c \in R^n$ represents the center of the basis, and r represents the radius of the basis. Learning data are used as the center of the basis. The output of the output layer elements is the linear sum of the products of the output from the respective intermediate element and the weight. The output O(x) of the output layer element is given by the following equation:

$$O(x) = \sum_{j=1}^{m} w_j h_j(x) \quad (2.2)$$

wherein m represents the number of intermediate layer elements, $w_j (j=1, \ldots, m)$ represents the weight by which the "m"th intermediate layer is multiplied. Thus, RBFN is a network which approximates a curved line or a curved surface by overlapping of the weighed bases.

Neural networks carry out learning in order to obtain the optimum output with respect to the given input. In RBFN, the output of the network is determined by the linear sum of the products of the output of the respective intermediate layer elements and the weight. Therefore, to obtain the optimum output, it is necessary to determine the optimum weight. Thus, the learning by RBFN necessitates the determination of the optimum weight. In RBFN, the optimum weight may be determined from the given data by solving the following linear equation (Non-patent Literature 7 and 8):

$$y = Hw \quad (2.3)$$

wherein $$y = \begin{bmatrix} y_1 \\ y_2 \\ \vdots \\ y_p \end{bmatrix}, H = \begin{bmatrix} h_1(x_1) & h_2(x_1) & \ldots & h_p(x_1) \\ h_1(x_2) & h_2(x_2) & \ldots & h_p(x_2) \\ \vdots & \vdots & \ddots & \vdots \\ h_1(x_p) & h_2(x_p) & \ldots & h_p(x_p) \end{bmatrix}, w = \begin{bmatrix} w_1 \\ w_2 \\ \vdots \\ w_p \end{bmatrix} \quad (2.4)$$

with the proviso that the number of the intermediate layer elements is the same as the number of elements of the input layer, and that the center of the basis is fixed. Thus, since the optimum weight can be determined by a simple matrix operation, RBFN is a high-speed method. Further, since the optimum weight is uniquely determined by the matrix operation, the solution does not depend on the initial value.

Although a well-known RBFN may be employed, it is preferred to introduce a basis-auto-optimization algorithm and weight-decay term-adding algorithm to the RBFN in order to simultaneously increase the estimation accuracy and the generalizing ability based on the chemical data which are small in number (the RBFN to which the basis-auto-optimization algorithm and weight-decay term-adding algorithm are introduced is hereinafter referred to as "improved RBFN" for convenience). This improved RBFN will now be described in more detail.

The improved RBFN is a neural network specialized in the analysis of chemical data, which generalizing ability is further strengthened. With the improved RBFN, the estimation accuracy for chemical data is increased by the basis-auto-optimization algorithm compared to the conventional method. Further, by adding a weight-decay term to the evaluation function of the network, the generalizing ability is increased compared to conventional methods. The basis-auto-optimization and the weight-decay term will now be described in detail.

Basis-Auto-Optimization

The concept of basis-auto-optimization is shown in FIG. 3. In the basis-auto-optimization, the number m of the intermediate layer elements is set to be equal to the number p of the data set. Furthermore, in the basis-auto-optimization, the optimum radius of the basis is automatically calculated depending on the data. In general, in RBFN, the number of intermediate layer elements is smaller than the number of data for learning, and the larger the number of the intermediate layer elements, the higher the complementation accuracy (Non-patent Literature 6). Thus, in cases where the number of data is small, it is preferred to provide the intermediate layer elements in the same number as the number of data. In view of the above, in the basis-auto-optimization, bases are used for all of the input data points. In the conventional RBFN, the basis radius is set equal in all bases. Although this is effective in cases where the data are uniformly distributed in the input space, this is not effective in cases where data are unevenly distributed. Although the uneven distribution of the data may be reduced by normalizing the data logarithmically or with an index, it is difficult to make the data uniformly distributed in the input space. Since the number of bases is small in the portions were the data are sparse, it is impossible to carry out an interpolation. In the portions in which the data are dense, multiple bases overlap, and lengthy bases are generated. That is, the network falls into a state wherein the performance of the network is insufficient. To increase the performance of the network, it is necessary to realize the following two points.

To increase the ability of interpolation in the portions in which the data are sparse To increase the estimation accuracy in the portions in which the data are dense To realize these, the basis radius is set to the distance between the centroid
$\bar{x}$
and the basis center $x_i$ in the basis-auto-optimization. In the basis-auto-optimization, the basis radius is determined for each basis according to the following equation:

$$r_i = \|x_i - \bar{x}\| \quad (2.5)$$

As described above, in the basis-auto-optimization, since all of the data for learning are used as basis centers, the number m of the intermediate layer elements is equal to the number of the data for learning. Therefore, $$r = (r_1, r_2, \ldots, r_p)$$

Furthermore,
$\bar{x}$
is the centroid of the input data, and expressed by $$\bar{x} = \frac{\sum_{i=1}^{p} x_i}{p} \quad (2.6)$$

By setting the basis radius to the distance between the centroid of the input data and the basis center, the basis radius is large in the portions where the data are sparse, and the basis radius is small in the portions where the data are dense. By this, the width of the basis is increased in the portions where the data are sparse, so that a large region can be interpolated by a single basis. On the other hand, the width of the basis is decreased in the portions where the data are dense, so that lengthy bases are not generated even if a number of bases are overlapped, and precise estimation may be attained. Thus, increase in the ability of interpolation in the portions in which the data are sparse and increase in the estimation accuracy in the portions in which the data are dense are simultaneously attained.

In cases where r is 0, the minimum value $r_{min}$ satisfying $r_i > 0$ among $r_i(i=0, \ldots, p)$ is employed as r.

The basis-auto-optimization suppresses the formation of a lengthy basis. In cases where the number of data is small, it is not necessary to select the optimum basis. However, in cases where the data are unevenly distributed, a lengthy basis is formed even if the number of data is small. This is proved as follows:

In RBFN, the output O(x) with respect to the input $x_i(1 \leq i \leq p)$ is represented by the following equation:

$$O(x_i) = w_1 h_1(x_i) + w_2 h_2(x_i) + \ldots + w_p h_p(x_i) \quad (2.7)$$

Here, paying attention to $h_k(x_i)$ and $h_l(x_i)$ ($l \neq k$), $$H' = w_1 h_1(x_i) + w_2 h_2(x_i) + \ldots + w_p h_p(x_i) - w_k h_k(x_i) - w_l h_l(x_i) \quad (2.8)$$

Here, Equation (2.7) can be expressed by the following equation:

$$O(x_i) = H' + w_k h_k(x_i) + w_l h_l(x_i) \quad (2.9)$$

If the data are unevenly distributed, bases which radii are close to each other and which intermediate layer outputs are almost equal, are generated. Assuming that the basis center of $h_k(x_i)$ and the basis center of $h_l(x_i)$ are closely located to each other, it is regarded that $h_k(x_i) = h_l(x_i)$. Assuming that $h_k(x_i) = h_l(x_i)$, Equation (2.9) can be expressed by the following equation:

$$O(x_i) = H' + (w_k + w_l) h_k(x_i) \quad (2.10)$$

Here, assuming that $w_k + w_l = w_k'$, Equation (2.10) can be expressed by the following equation:

$$O(x_i) = H' + w_k' h_k(x_i) \quad (2.11)$$

From Equation (2.11), it is seen that $h_l(x_i)$ is not necessary to express the output O(x).

As seen from the above, in cases where the data are unevenly distributed, lengthy bases are generated. In the basis-auto-optimization, since the basis radius is derived for each basis, it is unlikely that the intermediate layer outputs are equal even if the basis centers are close. Further, since the basis becomes narrow, overlapping of the bases is supressed. Therefore, in the improved RBFN, lengthy bases are more unlikely formed than in RBFN. That is, in the improved RBFN, the amount of lengthy calculations is decreased compared to RBFN.

Weight-Decay Term

Figure 4:
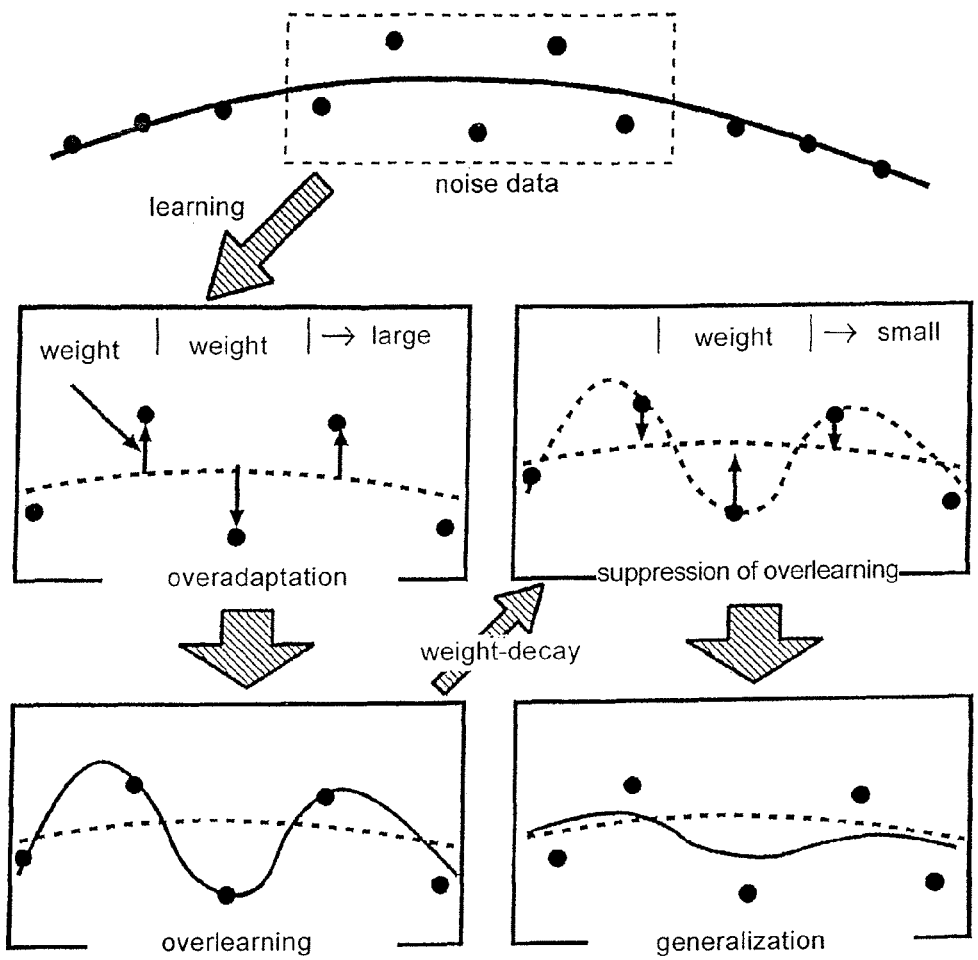
FIG. 4 explains the suppression of overlearning by the weight-decay term.

The objective of introducing the weight-decay term-adding algorithm is to increase the generalizing ability of the network. By adding the weight-decay term to the evaluation function of the network, excess adaptation of the weight to the data having noise is prevented. By this, the approximated curve or curved surface is smoothened, and overlearning is supressed with respect to noise-contaminated data. The concept of suppressing the overlearning by the weight-decay term is shown in FIG. 4.

In general, the evaluation function of the network in RBFN is expressed by the following equation:

$$E = \sum_{i=1}^{p} (y_i - O(x_i))^2 \quad (2.12)$$

with the proviso that the output is one-dimensional. Here, p is the number of data sets for learning, $(x_i, y_i)$ is the data set for learning.

If the network model earns noise-containing data, it falls into a state of overlearning. In general, noise-containing data are far from the ideal regression curve (or curved surface). Therefore, a network model which fell into a state of overlearning has a complicated shape. However, since Equation (2.12) lacks a term considering the complexity of the model, there is a problem in that the model becomes complicated and falls into overlearning (Non-patent Literature 8).

To avoid such a problem, it is necessary to add a term which suppresses the complexity of the model to the evaluation function of the network. In this invention, a weight-decay term is added to the evaluation function as the term for suppressing complication of the model. In this invention, the following equation is used as the weight-decay term to prevent excessive adaptation of the weight.

$$\lambda \sum_{i=1}^{p} w_i^2 \quad (2.13)$$

wherein λ is a positive number obtained experimentally. The evaluation function, to which the weight-decay term is added, can be expressed by the following equation:

$$E = \sum_{i=1}^{p} (y_i - O(x_i))^2 + \lambda \sum_{i=1}^{p} w_i^2 \quad (2.14)$$

The weight which minimizes this evaluation function is the optimum weight.

The weight-decay term is composed of the sum of squares of the weights. If the sum of squares of the weights is decreased, the overall absolute value is decreased. If the overall absolute value of the weights is decreased, the overall height of the bases multiplied by the weights is decreased. By this, excessive adaptation of the weights with respect to noise-contaminated data can be prevented.

If the weight excessively adapts to noise-contaminated data, as shown in FIG. 4, the slope of the approximated curve (curved surface) becomes steep. This occurs, because the basis is drawn in the positive or negative direction in order to try to adapt to the data. That is, if the absolute value of the weight is large, the network overlearns. Therefore, by virtue of the weight-decay term, the network learns in a way such that the absolute value of the weight is decreased.

If only a part of the weights excessively responds, the value of the weight-decay term is increased, and the value of Equation (2.14) is increased. Therefore, complication of the model may be prevented by minimizing the value of Equation (2.14). However, not all data are contaminated with noise. Furthermore, the size of the noise is also not known. Therefore, it is necessary to change the degree of influence of the weight-decay term based on the data. The parameter which changes the degree of influence of the weight-decay term is λ. By adjusting λ, the degree of influence of the weight-decay term can be optimized.

It will now be described how to obtain the weight when the weight-decay term is added.

First, Equation (2.14) is differentiated partly with respect to all of $w_j (j=1, \ldots, p)$.

$$\frac{\partial E}{\partial w_j} = 2\sum_{i=1}^{p}(O(x_i) - y_i)\frac{\partial O}{\partial w_j}(x_i) + 2\lambda w_j \quad (2.15)$$

Substituting $$\frac{\partial O}{\partial w_j}(x_i) = h_j(x_i)$$

in and after rearrangement, his equation is expressed as follows:

$$\sum_{i=1}^{p} O(x_i)h_j(x_i) + \lambda w_j = \sum_{i=1}^{p} y_i h_j(x_i) \quad (2.16)$$

Expressing this equation in the form of a matrix, $$h_j^T O + \lambda w_j = h_j^T y \quad (2.17)$$

where, $$h_j = \begin{bmatrix} h_j(x_1) \\ h_j(x_2) \\ \vdots \\ h_j(x_p) \end{bmatrix}, O = \begin{bmatrix} O_j(x_1) \\ O_j(x_2) \\ \vdots \\ O_j(x_p) \end{bmatrix}, y = \begin{bmatrix} y_1 \\ y_2 \\ \vdots \\ y_p \end{bmatrix} \quad (2.18)$$

and wherein $h^T$ is the transposed matrix. Summarizing over all of j, Equation (2.17) is expressed by the following equation:

$$H^T O + \lambda w = H^T y \quad (2.19)$$

where, $$H = \begin{bmatrix} h_1(x_1) & h_2(x_1) & \ldots & h_p(x_1) \\ h_1(x_2) & h_2(x_2) & \ldots & h_p(x_2) \\ \vdots & \vdots & \ddots & \vdots \\ h_1(x_p) & h_2(x_p) & \ldots & h_p(x_p) \end{bmatrix}, w = \begin{bmatrix} w_1 \\ w_2 \\ \vdots \\ w_p \end{bmatrix} \quad (2.20)$$

Substituting O=Hw in this equation, and after rearrangement, this equation is expressed as follows:

$$\begin{aligned} H^T y &= H^T O + \lambda w \\ &= H^T H w + \lambda w \\ &= (H^T H + \lambda)w \end{aligned} \quad (2.21)$$

From the above, the optimum weight is obtained by the following equation:

$$w = (H^T H + \lambda)^{-1} H^T y \quad (2.22)$$

In cases where the output is multidimensional, the optimum weight is obtained by the following equation which is an expansion of Equation (2.22).

$$W = (H^T H + \lambda)^{-1} H^T Y \quad (2.23)$$

$$W = \begin{bmatrix} w_{1,1} & w_{1,2} & \ldots & w_{1,k} \\ w_{2,1} & w_{2,2} & \ldots & w_{2,k} \\ \vdots & \vdots & \ddots & \vdots \\ w_{p,1} & w_{p,2} & \ldots & w_{p,k} \end{bmatrix}, Y = \begin{bmatrix} y_{1,1} & y_{1,2} & \ldots & y_{1,k} \\ y_{2,1} & y_{2,2} & \ldots & y_{2,k} \\ \vdots & \vdots & \ddots & \vdots \\ y_{p,1} & y_{p,2} & \ldots & y_{p,k} \end{bmatrix} \quad (2.24)$$

As described above, as the RBFN used in the method of the present invention, an improved RBFN comprising the basis-auto-optimization algorithm and the weight-decay term-adding algorithm is preferred.

In the preferred Examples described below, the first phase radial basis function neural network comprises a radial basis function neural network (1) into which the response value from the sensor measuring $Na^+$ is fed, and which calculates the $Na^+$ concentration; a radial basis function neural network (2) into which the response value from the sensor measuring $K^+$ is fed, and which calculates the $K^+$ concentration; a radial basis function neural network (3) into which the response value from the sensor measuring $Cl^-$ is fed, and which calculates the $Cl^-$ concentration; a radial basis function neural network (4) into which the response value from the sensor measuring $H^+$ is fed, and which calculates the pH; a radial basis function neural network (5) into which the response value from the sensor measuring sucrose, the response value from the sensor measuring glucose, and the pH are fed, and which calculates the sucrose and glucose concentrations; a radial basis function neural network (6) into which the response value from the sensor measuring glutamate and the pH are fed, and which calculates the glutamate concentration; and a radial basis function neural network (7) into which the response value from the sensor measuring caffeine is fed, and which calculates the caffeine concentration.

The learning process of the first phase RBFN can be carried out by obtaining response values from the respective sensors for mixtures containing known concentrations of the above-described taste-representing components, and feeding said response values and the actual concentrations of the respective taste-representing components into said first phase RBFNs. A preferred example is also described in detail in the Examples below.

In the next step, the concentrations of the respective taste-representing components, which concentrations were calculated by the first phase RBFN, are fed into the second phase RBFN to calculate the intensities of saltiness, sourness, sweetness, umami and bitterness sensed by humans. The second phase RBFN is an RBFN which correlates the concentrations of the respective components with the intensities of saltiness, sourness, sweetness, umami and bitterness sensed by humans. As the RBFN, an improved RBFN comprising the basis-auto-optimization algorithm and the weight-decay term-adding algorithm is preferred. The improved RBFN is as described above.

Since the second phase RBFN correlates the concentrations of the respective components and the intensities of saltiness, sourness, sweetness, umami and bitterness sensed by humans, a sensory test by panelists is carried out of course. The intensities of the saltiness, sourness, sweetness, umami and bitterness sensed by humans to be fed into the second phase RBFN when learning, are preferably those obtained by a method wherein panelists taste 5 standard samples, which independently represent saltiness, sourness, sweetness, umami and bitterness, respectively; then, the panelists taste a plurality of samples for learning, and sensorically evaluate the intensities of the 5 tastes, respectively; and the panelists express the evaluated intensities in terms of values by comparing the intensities with the intensity of each taste of the standard samples. More preferably, the standard samples consist of 2 standard samples for each taste, which have different concentrations, respectively, and the results of the sensory evaluation of the samples for learning are expressed in terms of values by rating on a 5-point scale which is: (1) no taste at all, (2) tastes weaker than the lower concentration standard sample, (3) tastes equally to the lower concentration standard sample, (4) taste is midpoint in between the lower concentration standard sample and the higher concentration standard sample, and (5) tastes equally to or stronger than the higher concentration standard sample. The intervals between the adjacent points may be further divided. Details thereof are described in the Examples below. By making the second phase RBFN to learn also the concentration of each component and the standard deviation of intensities of saltiness, sourness, sweetness, umami and bitterness sensed by humans, the variations in the intensities of saltiness, sourness, sweetness, umami and bitterness sensed by humans may also be calculated. Details thereof are described in the Examples below.

Since the second RBFN is made to learn the results of the sensory test by the panelists, the method of the present invention can closely simulate the human gustation. As will be concretely described in the Examples below, surprisingly, by the method of the present invention, illusions of taste, which are sensed by humans, such as that umami is increased as the salt increases, and that bitterness is decreased as sugars increase, were able to be reproduced. Further, since two-phase RBFNs, preferably improved RBFNs are used, accuracy is increased when compared to the method wherein the response values from the sensors are directly fed. Still further, by the method of the present invention, the second phase RBFN may be prepared for each group of different panelists. For example, by making the RBFN learn the results of the sensory test conducted by the panelists whose sex is the same or whose native place is the same, the gustation of the group of the particular panelists can be simulated. This is useful for the marketing of food products and beverages to the respective sexes or in the respective areas.

The present invention will now be described more concretely by means of examples thereof. It should be noted, however, that the present invention is not restricted to the Examples below.

EXAMPLES

1. Materials and Methods (1) Sensors $Na^+$, $K^+$ and $Cl^-$ were selected as the components representing saltiness; $H^+$ was selected as the component representing sourness; glucose and sucrose were selected as the components representing sweetness; glutamate was selected as the component representing umami; and caffeine was selected as the component representing bitterness. Sensors which can quantify these components, respectively, were prepared. The $Na^+$ sensor was a $Na^+$ ion-selective electrode using DD16C5 as a $Na^+$ ionophore. The $K^+$ sensor was a $K^+$ ion-selective electrode using valinomycin as a $K^+$ ionophore. The $Cl^-$ sensor was a $Cl^-$ ion selective electrode using bisthiourea-1 as a $Cl^-$ ionophore. The $H^+$ sensor was a $Pt/IrO_2$ pH electrode. The glucose electrode was an enzyme electrode using glucose oxidase as the enzyme. The sucrose sensor was an enzyme electrode using invertase, mutarotase and glucose oxidase as the enzymes. The glutamate sensor was an enzyme electrode using L-glutamate oxidase as the enzyme. All of the ionophores and enzymes were commercially available, and the electrodes were assembled by the conventional methods. The caffeine sensor was the electron cyclotron resonance (ECR-) sputtered carbon electrode manufactured by NTT Afty Corporation.

(2) First Phase RBFN

Figure 5:
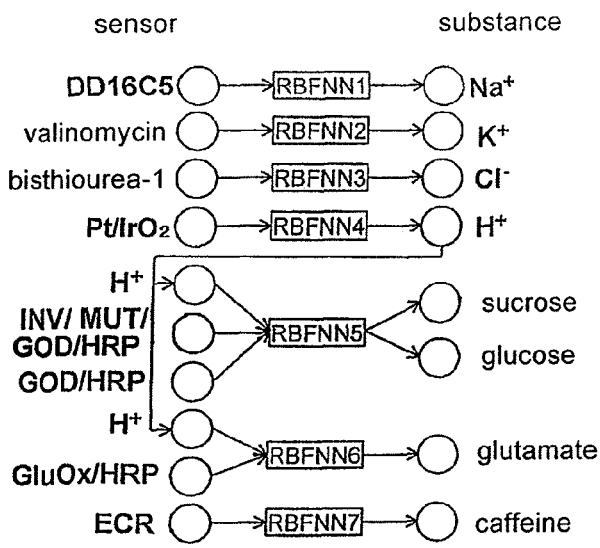
FIG. 5 shows the structure of the first phase RBFN.

The structure of the first phase RBFN is shown in FIG. 5. In this figure, "RBFNN" stands for radial basis function neural network, and has the same meaning as the RBFN described above. As shown in FIG. 5, the first phase RBFN comprises RBFNN1 into which the response value from the sensor measuring $Na^+$ is fed, and which calculates the $Na^+$ concentration; RBFNN2 into which the response value from the sensor measuring $K^+$ is fed, and which calculates the K+ concentration; RBFNN3 into which the response value from the sensor measuring $Cl^-$ is fed, and which calculates the $Cl^-$ concentration; RBFNN4 into which the response value from the sensor measuring $H^+$ is fed, and which calculates the pH; RBFNN5 into which the response value from the sensor measuring sucrose, the response value from the sensor measuring glucose, and the pH are fed, and which calculates the sucrose concentration and the glucose concentration; RBFNN6 into which the response value from the sensor measuring glutamate, and the pH are fed, and which calculates the glutamate concentration; and RBFNN7 into which the response value from the sensor measuring caffeine is fed, and which calculates the caffeine concentration. All of the RBFNs are the above-described improved RBFN. The reason to employ such a constitution is as follows: Since the sensors measuring $Na^+$, $K^+$, $Cl^-$, $H^+$ and caffeine, respectively, have high selectivity, one RBFN was allotted to each sensor so as to calculate the concentration of the single respective taste-representing component. On the other hand, glucose in the sample interferes with the sucrose electrode. Further, the enzyme activity changes depending on the pH. Therefore, into a single RBFN, the response value from the sucrose sensor, the response value from the glucose sensor and the response value from the pH sensor were fed, and the sucrose concentration and glucose concentration were obtained as output from the single RBFN. Similarly, in the case of the glutamate sensor, since the activity of glutamate oxidase is influenced by the pH, the response value from the pH sensor and the response value from the glutamate sensor were fed into a single RBFN.

The parameters of the respective RBFNs and the concentration ranges of the respective taste-presenting components in the standard samples used for learning are shown in Table 1.

TABLE 1

| Taste | Substance | Concentration Range in Sample | RBFNN Structure | | | |
|---|---|---|---|---|---|---|
| | | | Network | Number of Neurons | Learning Epoch | λ |
| Saltiness | $Na^+$ | 1-167 mM | RBFNN1 | 1 × 10 × 1 | 1 | 0.0001 |
| | $K^+$ | 1-167 mM | RBFNN2 | 1 × 10 × 1 | 1 | 0.0001 |
| Bitterness | $Cl^-$ | 1-167 mM | RBFNN3 | 1 × 10 × 1 | 1 | 0.0001 |
| | $H^+$ | pH 2.7-9.4 | RBFNN4 | 1 × 17 × 1 | 1 | 0.0001 |
| Umami | sucrose | 0-90 mM | RBFNN5 | 3 × 35 × 2 | 1 | 0.0001 |
| | glucose | 0-40 mM | | | | |
| Sweetness | glutamate | 0.005-5 mM | RBFNN6 | 2 × 36 × 1 | 1 | 0.0001 |
| Sourness | caffeine | 0.1-6.5 mM | RBFNN7 | 1 × 10 × 1 | 1 | 0.0001 |

The number of intermediate layers is equal to the number of the data sets used for the construction (learning) of the RBFN. The learning process, using standard samples having known concentrations, was carried out as follows: First, the learning data set of the input data and the teaching data were provided. As the learning data set, 7 types of data, that is, the data for $Na^+$, $K^+$, $Cl^-$, pH, sucrose and glucose, glutamate, and caffeine were provided. Here, the input data were the electric currents or electric potentials measured by the respective sensors, and the teaching data were the concentrations of the respective components contained in the standard samples, which resulted in the corresponding electric currents or electric potentials measured by the respective sensors. Each of these learning data sets was fed into the respective program, and the results of the cross validation were sequentially derived.

The evaluation of the RBFN was carried out by the cross validation based on the leave-one-out method. In this method, from N measurement samples, an arbitrary single sample is excluded. Using the response values of the remaining (N−1) samples, each RBFN is made to learn the relationship between the response value(s) and the concentration(s) of the component(s). By feeding the response value of the single sample, which was not used in the learning process, as a "response value of an unknown sample", the concentrations of the respective components contained in the sample are estimated. By comparing the output estimates and the concentrations of the components actually contained in the sample, the estimation ability of the RBFNs can be evaluated. Similar cross validation was carried out for all of the samples in each experiment, and the mean error of the N samples was calculated in terms of the root-mean-square error of prediction (RMSEP) and the average relative error (ARE).

(3) Second Phase RBFN

Figure 6:
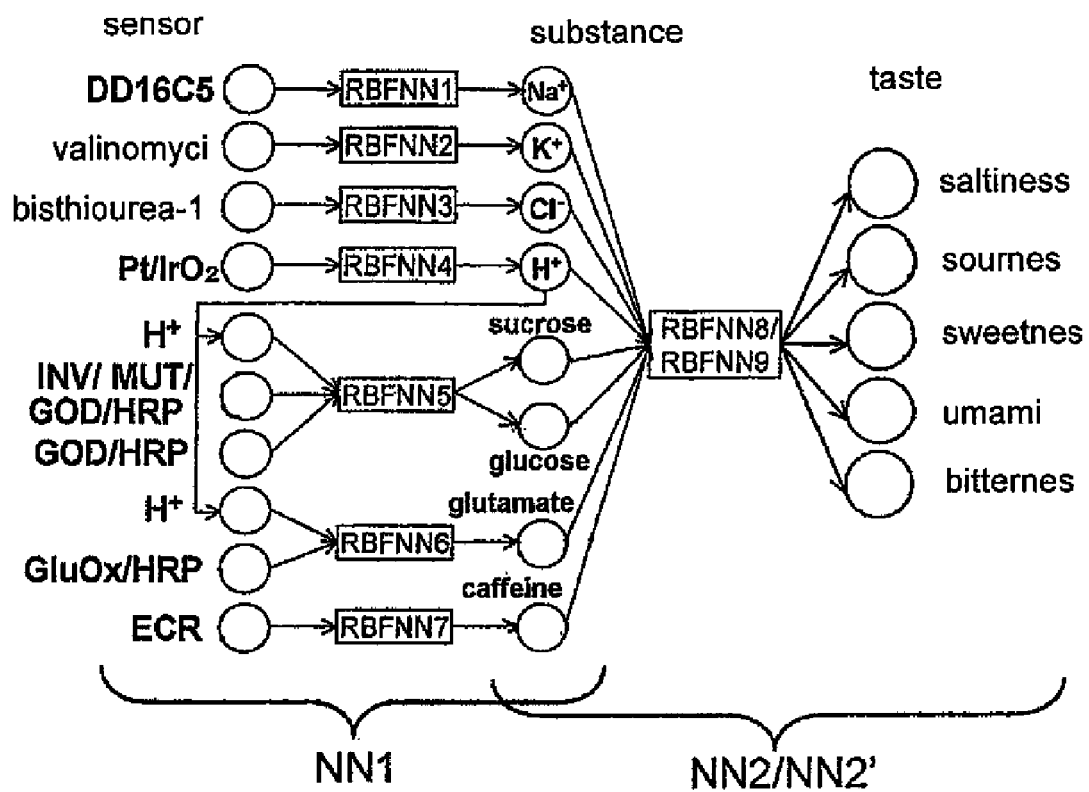
FIG. 6 shows the structure of the second phase RBFN.

The structure of the method of the Example, including the second phase RBFN, is shown in FIG. 6. As shown in FIG. 6, the concentrations of the respective taste-representing components calculated in the first phase are fed into one RBFN, and the intensities of the 5 basic tastes are obtained as output. RBFNN8 gives as outputs the averages of the intensities of the 5 basic tastes, and RBFNN9 gives as outputs the standard deviation for each basic taste.

To make it possible to accurately simulate human gustation, a sensory test with 51 panelists was carried out, and the results were used for learning. The sensory test with the panelists was carried out as follows: The standard samples for saltiness were solutions of 0.625 g and 1.875 g of table salt, respectively, in 100 mL of water, and the former was defined as level 3, and the latter was defined as level 5. The standard samples for sourness were solutions of 2.5 g and 7.5 g of vinegar, respectively, in 100 mL of water, and the former was defined as level 3, and the latter was defined as level 5. The standard samples for sweetness were solutions of 3 g and 9 g of sugar, respectively, in 100 mL of water, and the former was defined as level 3, and the latter was defined as level 5. The standard samples for umami were solutions of 0.125 g and 0.375 g of sodium glutamate (AJINOMOTO (registered trademark), respectively, in 100 mL of water, and the former was defined as level 3, and the latter was defined as level 5. The standard samples for bitterness were 50 mL of sugar-free coffee and 50 mL of sugar-free coffee to which 1.43 g of instant coffee was added, respectively, and the former was defined as level 3, and the latter was defined as level 5.

Samples for learning were: ionized alkaline water, soda water, green tea, seaweed tea, Oolong tea, coffee (sugar-free), black tea (sugar-free), black tea (sugar-added), apple juice, orange juice, vegetable juice, tomato juice, lemon juice (5-fold diluted), vinegar honey, softdrink (trademark "Calpis Water"), softdrink (trademark "coca cola"), melon soda, softdrink (trademark "Pocari Sweat"), softdrink (trademark "Aminoshiki"), milk, cocoa, softdrink (trademark "Oronamin C Drink"), noodle sauce, chicken soup, consomme soup, miso soup, Japanese clear soup, potage soup and ume brandy (2-fold diluted), totally 30 types of samples.

Each panelist tasted the standard samples, and memorized the level 3 and level 5 of each basic taste. Thereafter, they sequentially tasted the 30 types of samples for learning, and evaluated the intensities of the 5 basic tastes. For each taste, evaluation was performed by rating basically on a 5-point scale which is (1) no taste at all, (2) tastes weaker than the lower concentration standard sample, (3) tastes equally to the lower concentration standard sample, (4) taste is midpoint in between the lower concentration standard sample and the higher concentration standard sample, and (5) tastes equally to or stronger than the higher concentration standard sample, and intervals between the adjacent points were further divided into totally 10 points. The results were recorded in terms of numerical values. All of the samples were at room temperature, and each panelist rinsed the mouth before tasting the next sample. The averages and standard deviations of the obtained values were calculated.

On the other hand, the above-described 30 types of samples for learning were measured by the above-described sensors, and from the obtained response values, the concentrations of the respective taste-representing components calculated by the first phase RBFN were determined. These concentrations and the average values and standard deviations resulting from the above-described sensory test were made to be learned by the RBFN to constitute the second phase RBFN. In both RBFNN8 and RBFNN9, the number of neurons was 8×30×5, the learning epoch was 1, and $\lambda$ was 0.0001.

The second phase RBFN was also subjected to the cross validation based on the leave-one-out method in the same manner as described above.

(4) Simulation of Interactions Between Tastes

To confirm whether the above-described method succeeded in closely simulating the human gustation or not, interactions between tastes, that is, illusions of tastes were simulated.

(i) Reproduction Test of Suppression of Bitterness by Sweetness

In human gustation, sweetness suppresses bitterness. For example, the bitterness of coffee is mildened by adding sugar thereto, in spite of the fact that the concentration of caffeine remains unchanged. To study, whether the suppression of bitterness by sweetness can be measured by the above-described method or not, the following experiment was conducted: 2-fold diluted sugar-free coffee was measured by the above-described sensors, and the concentrations of the respective taste-representing components were calculated using the above-described first phase RBFN. The concentration values other than the pH were doubled to obtain the values of the respective taste-representing components in the undiluted coffee. The pH of coffee is not substantially changed even if the coffee is 2-fold diluted. Sugar was slowly added to the coffee in a concentration from 0 mM to 60 mM, and the outputs (intensities of the 5 basic tastes) from the second phase RBFN were monitored.

(ii) Reproduction Test of Increase of Umami by Saltiness

As an illusion of human gustation, umami is increased as the saltiness is increased. To study whether the increase in umami by saltiness can be measured by the above-described method or not, the following experiment was performed: 2-fold diluted miso soup was measured by the above-described sensors, and the concentrations of the respective taste-representing components were calculated using the above-described first phase RBFN. Among the 8 taste-representing components, the values of $Na^+$, $K^+$ and $Cl^-$, which are major causes of saltiness, were set to 0. Then, these salty components were added to the original concentration (100%), to increase these 3 values, and the outputs of the tastes during this process were monitored.

(5) Validation of Constructed RBFN

To verify whether the performance of the above-described two-phase improved RBFN is sufficient or not, the results of evaluation of tastes by this RBFN were compared with the measurement results of other chemical quantification methods.

To evaluate the first-phase RBFN, the results were compared with the results obtained by using an RBFN in which r was fixed, by using an RBFN which did not contain the weight-decay term $\lambda$, by using a conventional RBFN which did not contain any of them, and by using a method employing back propagation. The measurement errors were compared.

To evaluate the measurement accuracy of the second-phase RBFN, the results were compared with those obtained by a method wherein the tastes are measured by a single phase RBFN, that is, by a method wherein the tastes are measured by a single phase RBFN based on the response values from the sensors, and those obtained by multivariate regression analysis (MVR), which is a general statistical method. The measurement accuracy was compared based on the mean relative error obtained by cross validation. The source codes of the first-phase and second-phase neural networks used in the above-described Example are shown in FIG. 11 to FIG. 24.

II. Results

Figure 7:
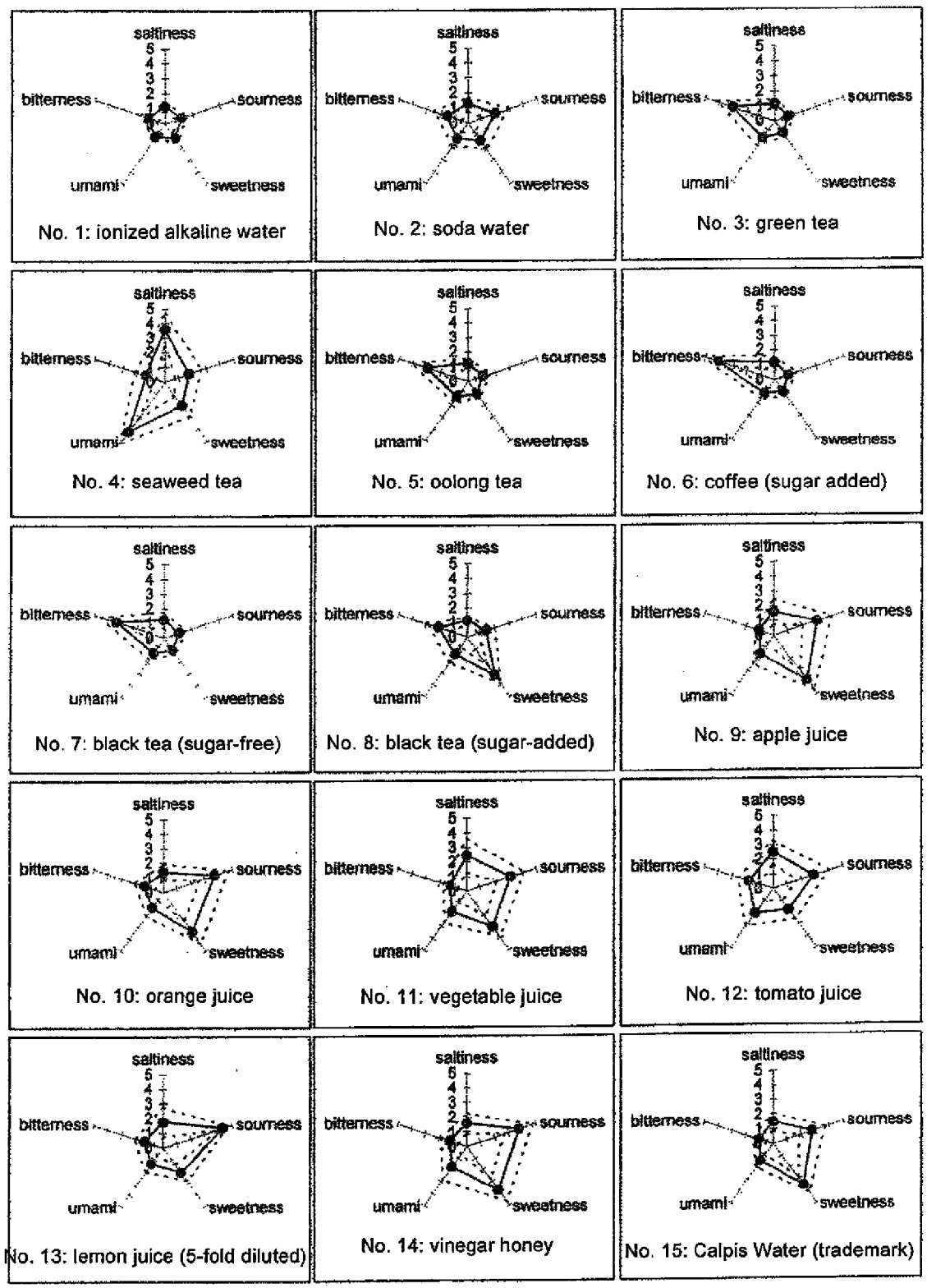
FIG. 7 shows the results of measurements obtained by subjecting various beverages to the method of the present invention.
Figure 8:
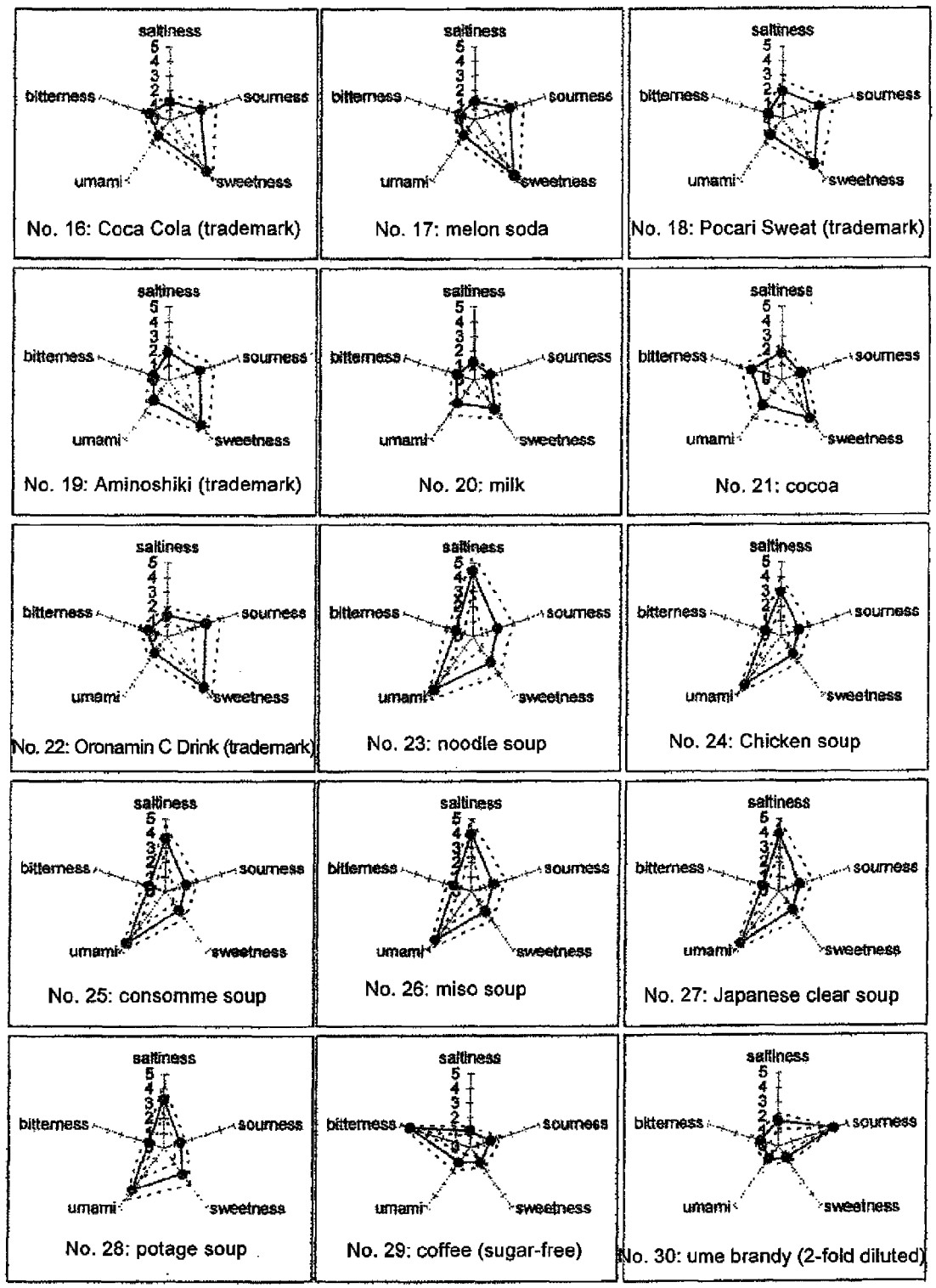
FIG. 8 shows the results of measurements obtained by subjecting various beverages to the method of the present invention.

The results of the cross validation of the first-phase RBFN are shown in Tables 2 and 3. A summary of the ARE and RMSEP is shown in Table 4. The results of the cross validation of the second-phase RBFN are shown in Table 5. The results of the measurements of the 30 types of samples for leaning used in the sensory test are shown in FIGS. 7 and 8. In FIGS. 7 and 8, solid lines indicate the average values of the results of measurements of tastes, and the dotted lines indicate the standard deviations thereof. From these, it was proved that the tastes of various beverages can be measured using the method of the Example described above.

TABLE 2

| Sample | Actual Concentration [mM] | Estimated Concentration [mM] | Relative Error [%] |
|---|---|---|---|
| | RBFNN1: $Na^+$ | | |
| 1 | 1.0 | 0.0 | 100.0 |
| 2 | 5.0 | 4.7 | 5.1 |
| 3 | 9.9 | 9.3 | 6.1 |
| 4 | 19.6 | 25.4 | 29.4 |
| 5 | 38.5 | 40.6 | 5.6 |
| 6 | 65.4 | 62.3 | 4.8 |
| 7 | 90.9 | 93.4 | 2.8 |
| 8 | 115.0 | 123.0 | 6.9 |
| 9 | 137.9 | 140.8 | 2.1 |
| 10 | 166.7 | 147.2 | 11.7 |
| | | ARE [%] | 17.4 |
| | | RMSEP [mM] | 7.1 |
| | RBFNN2: $K^+$ | | |
| 1 | 1.0 | 1.8 | 81.1 |
| 2 | 5.0 | 0.3 | 94.8 |
| 3 | 9.9 | 11.3 | 14.5 |
| 4 | 19.6 | 19.8 | 0.9 |
| 5 | 38.5 | 42.0 | 9.2 |
| 6 | 65.4 | 71.3 | 9.0 |
| 7 | 90.9 | 88.3 | 2.9 |
| 8 | 115.0 | 113.4 | 1.4 |
| 9 | 137.9 | 142.6 | 3.4 |
| 10 | 166.7 | 143.5 | 13.9 |
| | | ARE [%] | 23.1 |
| | | RMSEP [mM] | 8.0 |
| | RBFNN3: $Cl^-$ | | |
| 1 | 1.0 | 0.0 | 100.0 |
| 2 | 5.0 | 7.1 | 42.5 |
| 3 | 9.9 | 7.4 | 25.0 |
| 4 | 19.6 | 27.1 | 38.4 |
| 5 | 38.5 | 40.5 | 5.2 |
| 6 | 65.4 | 65.7 | 0.5 |

TABLE 2-continued

| Sample | Actual Concentration [mM] | Estimated Concentration [mM] | Relative Error [%] |
|---|---|---|---|
| 7 | 90.9 | 94.9 | 4.4 |
| 8 | 115.0 | 115.4 | 0.3 |
| 9 | 137.9 | 143.8 | 4.2 |
| 10 | 166.7 | 150.3 | 9.8 |
| | | ARE [%] | 23.0 |
| | | RMSEP [mM] | 6.2 |
| RBFNN4: $H^+$ | | | |
| 1 | 2.72 | 2.74 | 0.64 |
| 2 | 3.01 | 3.02 | 0.24 |
| 3 | 3.44 | 3.38 | 1.67 |
| 4 | 4.41 | 4.50 | 2.11 |
| 5 | 4.75 | 4.69 | 1.36 |
| 6 | 5.13 | 5.13 | 0.06 |
| 7 | 5.38 | 5.35 | 0.53 |
| 8 | 5.77 | 5.48 | 4.99 |
| 9 | 6.07 | 5.84 | 3.79 |
| 10 | 6.48 | 6.14 | 5.31 |
| 11 | 6.89 | 6.91 | 0.28 |
| 12 | 7.24 | 7.22 | 0.27 |
| 13 | 7.65 | 7.74 | 1.14 |
| 14 | 7.96 | 7.97 | 0.08 |
| 15 | 8.37 | 8.18 | 2.31 |
| 16 | 8.68 | 8.97 | 3.34 |
| 17 | 9.43 | 8.69 | 7.84 |
| | | ARE [%] | 2.11 |
| | | RMSEP [mM] | 0.24 |

TABLE 3

RBFNN5: sucrose/glucose

| | | Actual Concentration [mM] | | Estimated Concentration [mM] | | Relative Error [%] | |
|---|---|---|---|---|---|---|---|
| Sample | pH | sucrose | glucose | sucrose | glucose | sucrose | glucose |
| 1 | 3.35 | 0.0 | 1.0 | 2.6 | 0.2 | 2.6 | 81.7 |
| 2 | 3.35 | 1.0 | 2.5 | 1.4 | 2.8 | 37.3 | 11.4 |
| 3 | 3.35 | 5.0 | 5.0 | 8.7 | 9.3 | 76.2 | 87.4 |
| 4 | 3.35 | 46.7 | 18.7 | 35.8 | 19.9 | 23.3 | 6.5 |
| 5 | 3.35 | 87.0 | 43.5 | 26.6 | 12.7 | 67.2 | 70.9 |
| 6 | 4.17 | 2.0 | 0.0 | 1.4 | 0.0 | 30.2 | 0.0 |
| 7 | 4.17 | 5.0 | 1.0 | 1.4 | 0.2 | 72.7 | 76.3 |
| 8 | 4.17 | 9.9 | 2.5 | 4.2 | 3.3 | 57.3 | 32.3 |
| 9 | 4.17 | 11.8 | 4.9 | 16.2 | 8.7 | 37.4 | 77.6 |
| 10 | 4.17 | 46.7 | 18.7 | 96.2 | 24.8 | 105.9 | 32.6 |
| 11 | 5.00 | 9.9 | 0.0 | 1.2 | 0.0 | 37.8 | 0.0 |
| 12 | 5.00 | 9.8 | 6.9 | 19.6 | 9.1 | 99.4 | 32.9 |
| 13 | 5.00 | 19.5 | 7.8 | 17.3 | 10.2 | 11.2 | 30.8 |
| 14 | 5.00 | 37.9 | 14.2 | 50.7 | 15.2 | 33.6 | 6.9 |
| 15 | 5.00 | 89.3 | 17.9 | 37.9 | 13.7 | 57.5 | 23.1 |
| 16 | 6.08 | 1.0 | 0.0 | 1.6 | 0.0 | 57.5 | 0.0 |
| 17 | 6.08 | 10.9 | 2.5 | 7.3 | 3.0 | 32.6 | 19.8 |
| 18 | 6.08 | 10.8 | 7.4 | 23.8 | 14.5 | 120.1 | 96.3 |
| 19 | 6.08 | 14.6 | 9.8 | 17.8 | 12.1 | 21.4 | 23.7 |
| 20 | 6.08 | 24.0 | 14.4 | 14.8 | 8.6 | 38.6 | 40.3 |
| 21 | 7.15 | 14.8 | 1.0 | 0.2 | 2.0 | 98.3 | 98.4 |
| 22 | 7.15 | 19.5 | 4.9 | 45.7 | 22.2 | 134.0 | 355.7 |
| 23 | 7.15 | 33.5 | 9.6 | 43.6 | 15.9 | 30.3 | 65.8 |
| 24 | 7.15 | 42.3 | 18.8 | 44.2 | 15.8 | 4.5 | 15.8 |
| 25 | 7.15 | 87.3 | 39.3 | 31.6 | 11.7 | 63.8 | 70.1 |
| 26 | 8.17 | 0.0 | 1.0 | 4.7 | 1.0 | 4.7 | 2.4 |
| 27 | 8.17 | 0.0 | 7.4 | 8.2 | 13.3 | 8.2 | 78.8 |
| 28 | 8.17 | 4.9 | 9.9 | 4.9 | 14.7 | 1.0 | 49.6 |
| 29 | 8.17 | 4.9 | 19.5 | 6.0 | 14.0 | 22.2 | 28.0 |
| 30 | 8.17 | 9.6 | 28.8 | 5.3 | 13.0 | 44.9 | 55.1 |
| 31 | 8.99 | 1.0 | 14.8 | 12.5 | 16.3 | 1169.2 | 10.5 |
| 32 | 8.99 | 4.9 | 14.7 | 9.0 | 15.5 | 83.5 | 5.2 |
| 33 | 8.99 | 19.3 | 14.5 | 6.4 | 15.2 | 67.0 | 5.0 |
| 34 | 8.99 | 33.2 | 19.0 | 8.1 | 17.6 | 75.6 | 7.3 |
| 35 | 8.99 | 88.9 | 22.2 | 7.4 | 19.4 | 91.6 | 12.5 |

| | sucrose | glucose |
|---|---|---|
| ARE [%] | 84.8 | 46.0 |
| RMSEP [mM] | 24.6 | 8.6 |

RBFNN6: glutamate

| Sample | pH | Actual Concentration [mM] | Estimated Concentration [mM] | Relative Error [%] |
|---|---|---|---|---|
| 1 | 3.35 | 0.05 | 0.03 | 41.8 |
| 2 | 3.35 | 0.20 | 0.21 | 7.5 |
| 3 | 3.35 | 0.68 | 2.73 | 300.2 |
| 4 | 3.35 | 2.12 | 2.21 | 4.4 |
| 5 | 3.35 | 4.86 | 1.27 | 73.9 |
| 6 | 4.17 | 0.00 | 0.02 | 264.0 |

TABLE 3-continued

| | | | | |
|---|---|---|---|---|
| 7 | 4.17 | 0.02 | 0.01 | 53.9 |
| 8 | 4.17 | 0.52 | 0.41 | 19.8 |
| 9 | 4.17 | 0.91 | 1.03 | 12.8 |
| 10 | 4.17 | 1.49 | 0.77 | 48.3 |
| 11 | 5.00 | 0.10 | 0.07 | 32.6 |
| 12 | 5.00 | 0.20 | 0.20 | 3.5 |
| 13 | 5.00 | 0.34 | 0.37 | 10.3 |
| 14 | 5.00 | 0.50 | 0.70 | 39.6 |
| 15 | 5.00 | 1.62 | 3.19 | 96.3 |
| 16 | 5.00 | 3.26 | 2.17 | 33.3 |
| 17 | 6.08 | 0.03 | 0.03 | 1.8 |
| 18 | 6.08 | 0.29 | 0.36 | 23.7 |
| 19 | 6.08 | 1.25 | 2.27 | 82.0 |
| 20 | 6.08 | 3.11 | 2.76 | 11.4 |
| 21 | 6.08 | 4.91 | 3.17 | 35.4 |
| 22 | 7.15 | 0.10 | 0.08 | 18.7 |
| 23 | 7.15 | 0.20 | 0.23 | 16.8 |
| 24 | 7.15 | 0.68 | 1.19 | 74.5 |
| 25 | 7.15 | 2.12 | 4.10 | 93.8 |
| 26 | 7.15 | 3.96 | 2.32 | 41.5 |
| 27 | 8.17 | 0.05 | 0.02 | 51.0 |
| 28 | 8.17 | 0.20 | 0.33 | 66.3 |
| 29 | 8.17 | 0.68 | 1.88 | 175.5 |
| 30 | 8.17 | 1.64 | 1.75 | 6.5 |
| 31 | 8.17 | 3.05 | 1.44 | 52.8 |
| 32 | 8.99 | 0.01 | 0.03 | 158.2 |
| 33 | 8.99 | 0.10 | 0.10 | 3.4 |
| 34 | 8.99 | 1.08 | 2.32 | 115.5 |
| 35 | 8.99 | 2.04 | 1.85 | 9.3 |
| 36 | 8.99 | 4.81 | 1.43 | 70.3 |
| | | | ARE [%] | 59.7 |
| | | | RMSEP [mM] | 1.2 |

RBFNN7: caffeine

| Sample | Actual Concentration [mM] | Estimated Concentration [mM] | Relative Error [%] |
|---|---|---|---|
| 1 | 0.10 | 0.21 | 114.5 |
| 2 | 0.30 | 0.25 | 17.6 |
| 3 | 0.50 | 0.38 | 22.9 |
| 4 | 0.70 | 0.81 | 16.5 |
| 5 | 0.99 | 0.98 | 0.9 |
| 6 | 1.48 | 1.33 | 9.9 |
| 7 | 1.96 | 1.69 | 13.6 |
| 8 | 2.91 | 3.34 | 14.7 |
| 9 | 4.76 | 4.85 | 1.8 |
| 10 | 6.54 | 2.55 | 61.0 |
| | | ARE [%] | 27.3 |
| | | RMSEP [mM] | 1.3 |

TABLE 4

Results of Cross Validation of RBFNNs

| RBFNN | Substance | Concentration in Foods | Concentration Range in Sample | Average Relative Error [%] | RMSEP [mM] |
|---|---|---|---|---|---|
| RBFNN1 | $Na^+$ | 10-200 mM | 1-167 mM | 17.4 | 7.12 |
| | | | | 7.8 (1 < x < 140 mM) | 3.74 |
| RBFNN2 | $K^+$ | 10-200 mM | 1-167 mM | 23.1 | 7.99 |
| | | | | 17.0 (1 < x < 140 mM) | 3.39 |
| RBFNN3 | $Cl^-$ | 10-200 mM | 1-167 mM | 23.0 | 6.23 |
| | | | | 15.1 (1 < x < 140 mM) | 3.69 |
| RBFNN4 | $H^+$ | pH 2.5-9.0 | pH 2.7-9.4 | 2.11 | 0.24 |
| | | | | 1.76 (pH 2.7 < x < 9) | 0.16 |
| RBFNN5 | sucrose | 10-200 mM | 0-90 mM | 84.8 | 24.6 |
| | glucose | 20-100 mM | 0-40 mM | 46.0 | 8.63 |
| RBFNN6 | glutamate | 0.01-20 mM | 0.005-5 mM | 59.7 | 1.17 |
| RBFNN7 | caffeine | 0.7-5.0 mM | 0.1-6.5 mM | 27.3 | 1.27 |
| | | | | 12.2 (0.1 < x < 5 mM) | 0.19 |

TABLE 5

| Taste | NN2: Estimated Average | | NN2': Estimated Standard Deviation | | Mean Standard Deviation |
|---|---|---|---|---|---|
| | ARE [%] | RMSEP | ARE [%] | RMSEP | |
| Saltiness | 5.9 | 0.18 | 8.4 | 0.10 | 0.66 |
| Sourness | 7.2 | 0.19 | 10.9 | 0.19 | 0.82 |
| Sweetness | 12.4 | 0.72 | 8.2 | 0.17 | 0.74 |
| Umami | 5.6 | 0.18 | 8.4 | 0.11 | 0.76 |
| Bitterness | 3.9 | 0.15 | 9.6 | 0.11 | 0.62 |

Figure 9:
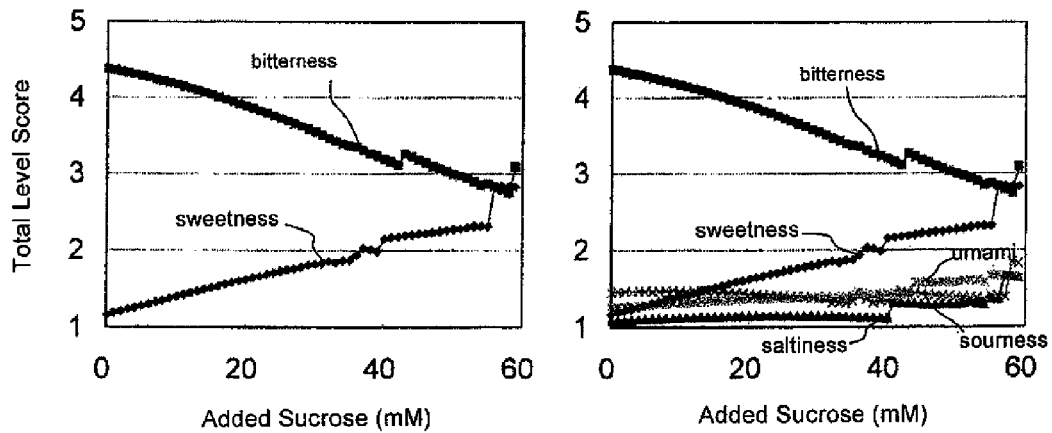
FIG. 9 shows the decrease in bitterness by addition of sucrose, which was measured by the method of the present invention.

The results of the reproduction test of suppression of bitterness by sweetness described above are shown in FIG. 9. The left figure in FIG. 9 shows only the sweetness and bitterness, and the right figure shows all of the 5 basic tastes. As is apparent from the left figure of FIG. 9, as the sucrose concentration increased, the measured sweetness increased and the bitterness decreased. As shown in the right figure, the other 3 basic tastes did not change. From these results, it was proved that the illusion of human gustation, that is, suppression of bitterness by sweetness, can also be reproduced by the method described above. From this, it is seen that the above-described method sophisticatedly simulates the human gustation.

Figure 10:
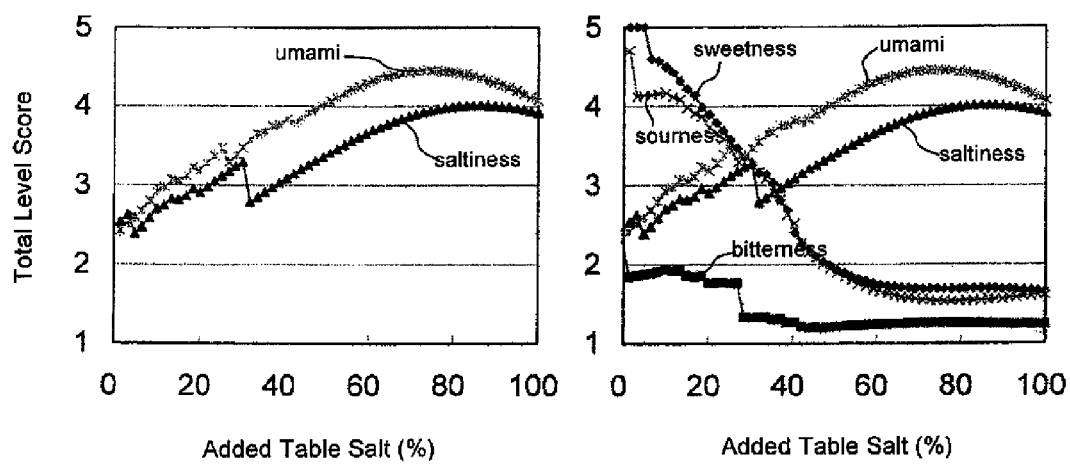
FIG. 10 shows the increase in umami by addition of table salt which was measured by the method of the present invention.

The results of the reproduction test of the increase in umami by saltiness are shown in FIG. 10. The left figure of FIG. 10 shows only the saltiness and umami, and the right figure shows all of the 5 basic tastes. As is apparent from the left figure of FIG. 10, as the added table salt increased, umami also increased in the same manner as saltiness. From these results, it was proved that the illusion of human gustation, that is, increase in umami by saltiness, can also be reproduced by the method described above. From this, it is seen that the above-described method sophisticatedly simulates the human gustation.

The AREs obtained by the above-described method of the present invention using the first-phase and second-phase RBFNs, by using an RBFN in which r was fixed, by using an RBFN which did not contain the weight-decay term X, by using a conventional RBFN which did not contain any of them, and by using a method employing back propagation, respectively, are shown in Table 6 (first-phase) and Table 7 (second-phase). From these results, it was proved that the ARE by the improved RBFN was smaller than those obtained by other RBFN, back propagation, single phase RBFN and MVR analysis, respectively.

TABLE 6

| | Average Relative Error [%] | | | |
|---|---|---|---|---|
| NN1 | This Example | RBFNN (fixed r) | RBFNN (no λ) | BPNN |
| $Na^+$ | 17.4 | 28.5 | 103.8 | 27.7 |
| $K^+$ | 23.1 | 28.5 | 39.7 | 19.4 |
| $Cl^-$ | 23.0 | 32.0 | 183.1 | 19.5 |
| $H^+$ | 2.1 | 5.2 | 19.5 | 2.5 |
| sucrose | 84.8 | 97.0 | 1289.8 | 371.1 |
| glucose | 46.0 | 52.2 | 3581.1 | 198.0 |
| glutamate | 59.7 | 71.4 | 168.3 | 137.0 |
| caffeine | 22.0 | 29.3 | 51.3 | 37.5 |
| Average | 34.8 | 43.0 | 680.0 | 101.6 |

TABLE 7

| | Average Relative Error [%] | | |
|---|---|---|---|
| NN2 | This Example | single-phase RBFNN | MVR Analysis |
| Saltiness | 5.9 | 17.6 | 16.2 |
| Sourness | 7.2 | 22.1 | 19.6 |
| Sweetness | 12.4 | 47.2 | 41.9 |
| Umami | 5.6 | 17.8 | 15.0 |
| Bitterness | 3.9 | 22.7 | 20.2 |
| Average | 7.0 | 25.5 | 22.6 |

The invention claimed is:

1. A computer-implemented method for measuring tastes, said method comprising the steps of:
    subjecting a test sample to measurements by sensors comprising electrodes, each sensor can quantify at least one component representing, individually or cooperatively, the taste of saltiness, sourness, sweetness, umami or bitterness, to obtain a response value from each sensor;
    inputting each of the obtained response values into a first phase radial basis function neural network, which correlates each response value with a concentration of each of the components and calculates the concentration of each component from each response value;
    inputting the calculated concentration of each component into a second phase radial basis function neural network, which correlates the calculated concentration of each component and the intensities of saltiness, sourness, sweetness, umami and bitterness sensed by humans, to calculate the intensities of saltiness, sourness, sweetness, umami and bitterness sensed by humans; and
    outputting the intensities as the measured taste.

2. The method according to claim 1, wherein said first and second phase radial basis function neural network comprises a basis-auto-optimization algorithm and a weight-repressing decay term-adding algorithm.

3. The method according to claim 1 or 2, wherein $Na^+$, $K^+$ and $Cl^-$ are selected as the components representing saltiness; $H^+$ is selected as the component representing sourness; glucose and sucrose are selected as the components representing sweetness; glutamate is selected as the component representing umami; and caffeine is selected as the component representing bitterness; and sensors for measuring these eight components are used.

4. The method according to claim 3, wherein said first phase radial basis function neural network comprises:
    a radial basis function neural network (1) into which the response value from the sensor measuring $Na^+$ is input, and which calculates the $Na^+$ concentration;
    a radial basis function neural network (2) into which the response value from the sensor measuring $K^+$ is input, and which calculates the $K^+$ concentration;
    a radial basis function neural network (3) into which the response value from the sensor measuring $Cl^-$ is input, and which calculates the $Cl^-$ concentration;
    a radial basis function neural network (4) into which the response value from the sensor measuring $H^+$ is input, and which calculates the pH;
    a radial basis function neural network (5) into which the response value from the sensor measuring sucrose, the response value from the sensor measuring glucose, and the pH are input, and which calculates the sucrose and glucose concentrations;

a radial basis function neural network (6) into which the response value from the sensor measuring glutamate and the pH are input, and which calculates the glutamate concentration; and a radial basis function neural network (7) into which the response value from the sensor measuring caffeine is input, and which calculates the caffeine concentration.

5. The method according to claim 1, wherein said intensities of the saltiness, sourness, sweetness, umami and bitterness sensed by humans are those obtained by a method wherein panelists taste five standard samples, which independently represent saltiness, sourness, sweetness, umami and bitterness, respectively; then the panelists taste a plurality of samples for learning and sensorically evaluate the intensities of said five tastes, respectively; and the panelists express the evaluated intensities in terms of numerical values by comparing the intensities with the intensity of each taste of said standard samples.

6. The method according to claim 5, wherein said standard samples consist of two standard samples for each taste, which have different concentrations, respectively, and the results of said sensory evaluation of said samples for learning are expressed in terms of values by rating on a 5-point scale which is (1) no taste at all, (2) tastes weaker than the lower concentration standard sample, (3) tastes equally to the lower concentration standard sample, (4) tastes equal to between the lower concentration standard sample and the higher concentration standard sample, and (5) tastes equal to or stronger than the higher concentration standard sample.

7. The method according to claim 1, wherein said second phase radial basis function neural network also correlates the concentration of each component with the standard deviation of intensities of saltiness, sourness, sweetness, umami and bitterness sensed by humans, and calculates variations in the intensities of saltiness, sourness, sweetness, umami and bitterness sensed by humans.

8. The method according to claim 1, said taste sensor comprising sensors, each of which sensors can quantify at least one component representing, individually or cooperatively, the taste of saltiness, sourness, sweetness, umami or bitterness, to obtain a response value from each sensor.

9. An apparatus for measuring tastes, said apparatus comprising said taste sensor according to claim 8 and a computer that stores and executes a computer program that performs the method of claim 8.

* * * * *